(12) United States Patent
Wolgast et al.

(10) Patent No.: US 9,102,627 B2
(45) Date of Patent: *Aug. 11, 2015

(54) PROCESSES FOR PREPARING 3-BENZAZEPINES

(75) Inventors: Beverly L. Wolgast, San Diego, CA (US); Charles A. Gilson, III, San Diego, CA (US); Shelley Aytes, San Diego, CA (US); Scott A. Estrada, La Jolla, CA (US); Dipanjan Sengupta, San Diego, CA (US); Brian Smith, San Diego, CA (US); Max Rey, Wallisellen (CH); Heidedore Jlsabeth Rey-Papina, legal representative, Wallisellen (CH); Ulrich Weigl, Hilzingen (DE)

(73) Assignee: Arena Pharmaceuticals, Inc., San Diego ( * ) Notice: Subject to any disclaimer, the term of this patent is extended or adjusted under 35 U.S.C. 154(b) by 0 days.

This patent is subject to a terminal disclaimer.

(21) Appl. No.: 13/619,788

(22) Filed: Sep. 14, 2012

(65) Prior Publication Data

US 2013/0165648 A1 Jun. 27, 2013

Related U.S. Application Data

(63) Continuation of application No. 10/560,953, filed as application No. PCT/US2004/019279 on Jun. 16, 2004, now Pat. No. 8,367,657.

(60) Provisional application No. 60/479,280, filed on Jun. 17, 2003, provisional application No. 60/512,967, filed on Oct. 21, 2003.

(51) Int. Cl.

| | | |
|---|---|---|
| *A61K 31/55* | (2006.01) | |
| *C07D 223/16* | (2006.01) | |
| *C07D 401/02* | (2006.01) | |
| *C07D 403/02* | (2006.01) | |
| *C07C 209/50* | (2006.01) | |
| *C07C 211/29* | (2006.01) | |
| *C07C 213/02* | (2006.01) | |
| *C07C 215/08* | (2006.01) | |
| *C07C 231/02* | (2006.01) | |
| *C07C 17/16* | (2006.01) | |
| *C07C 25/06* | (2006.01) | |
| *C07C 209/74* | (2006.01) | |
| *C07C 211/27* | (2006.01) | |

(52) U.S. Cl.
CPC .............. *C07D 223/16* (2013.01); *C07C 17/16* (2013.01); *C07C 25/06* (2013.01); *C07C 209/50* (2013.01); *C07C 209/74* (2013.01); *C07C 211/27* (2013.01); *C07C 211/29* (2013.01); *C07C 213/02* (2013.01); *C07C 215/08* (2013.01); *C07C 231/02* (2013.01)

(58) Field of Classification Search
CPC .... A61K 31/55; C07D 223/16; C07D 401/02; C07D 403/02

USPC ........ 514/212.02, 215, 217.01; 540/543, 586, 540/594
See application file for complete search history.

(56) References Cited

U.S. PATENT DOCUMENTS

| | | |
|---|---|---|
| 2,900,415 A | 8/1959 | Biel et al. |
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,541,954 A | 9/1985 | Borowski et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,856,503 A | 1/1999 | Aebi et al. |
| 5,861,393 A | 1/1999 | Danilewicz et al. |
| 5,925,651 A | 7/1999 | Hutchinson |
| 5,939,415 A | 8/1999 | Laufer et al. |
| 5,942,535 A | 8/1999 | Laufer et al. |
| 5,958,543 A | 9/1999 | Teng et al. |

(Continued)

FOREIGN PATENT DOCUMENTS

| | | |
|---|---|---|
| AU | 515236 | 1/1988 |
| CA | 1090797 | 12/1980 |

(Continued)

OTHER PUBLICATIONS

U.S. Appl. No. 60/479,280, filed Jun. 17, 2003, Aytes et al.
U.S. Appl. No. 60/512,967, filed Oct. 21, 2003, Aytes et al.
U.S. Appl. No. 60/789,191, filed Apr. 3, 2006, Freifeld et al.
U.S. Appl. No. 61/268,930, filed Jun. 18, 2009, Carlos et al.
Baindur et al., "(+)-3-allyl-7-halo-8-hydroxy-1-phenyl-2,3,4,5-tetrahydro-1H-3-benzazepines as Selective High Affinity D1 Dopamine Receptor Antagonists: Synthesis and Structure-Activity Relationship," J. Med. Chem., 35:67-72 (1992).

(Continued)

*Primary Examiner* — Brenda Coleman

(57) ABSTRACT

The present invention provides processes and intermediates for the preparation of 3-benzazepines and salts thereof which can be useful as serotonin (5-HT) receptor agonists for the treatment of, for example, central nervous system disorders such as obesity.

18 Claims, No Drawings

(56) References Cited

U.S. PATENT DOCUMENTS

| | | | |
|---|---|---|---|
| 5,958,943 | A | 9/1999 | Laufer et al. |
| 6,087,346 | A | 7/2000 | Glennon et al. |
| 6,218,385 | B1 | 4/2001 | Adam et al. |
| 6,900,313 | B2 | 5/2005 | Wasserscheid et al. |
| 6,953,787 | B2 | 10/2005 | Smith et al. |
| 6,972,295 | B2 | 12/2005 | Hagmann et al. |
| 7,514,422 | B2 | 4/2009 | Smith et al. |
| 7,704,993 | B2 | 4/2010 | Smith et al. |
| 7,977,329 | B2 | 7/2011 | Smith et al. |
| 8,168,782 | B2 * | 5/2012 | Weigl et al. ............... 540/594 |
| 8,299,241 | B2 * | 10/2012 | Gharbaoui et al. ........ 540/594 |
| 2007/0060568 | A1 | 3/2007 | Smith et al. |
| 2007/0275949 | A1 | 11/2007 | Smith et al. |
| 2009/0143576 | A1 | 6/2009 | Weigl et al. |
| 2010/0004223 | A1 | 1/2010 | Agarwal et al. |
| 2010/0173894 | A1 | 7/2010 | Smith et al. |

FOREIGN PATENT DOCUMENTS

| | | |
|---|---|---|
| CA | 2197789 A1 | 2/1996 |
| CH | 500194 | 1/1971 |
| DE | 1 944 121 | 3/1970 |
| DE | 19 14 456 | 6/1971 |
| DE | 33 15 106 A1 | 11/1983 |
| DE | 34 18 270 A1 | 11/1985 |
| EP | 0 007 070 B1 | 1/1983 |
| EP | 0 161 350 A1 | 11/1985 |
| EP | 0 174 118 A2 | 3/1986 |
| EP | 0 800 779 B1 | 7/1986 |
| EP | 0 204 349 A2 | 12/1986 |
| EP | 0 096 838 B1 | 4/1987 |
| EP | 0 285 287 A3 | 10/1988 |
| EP | 0 285 919 A1 | 10/1988 |
| EP | 0 987 235 B1 | 3/2003 |
| EP | 1 074 549 B1 | 11/2003 |
| GB | 1 196 229 | 6/1970 |
| GB | 1 221 324 | 2/1971 |
| GB | 1 225 053 | 3/1971 |
| GB | 1 247 306 | 9/1971 |
| GB | 1 268 243 | 3/1972 |
| GB | 1 599 705 | 10/1981 |
| GB | 2 133 401 A | 7/1984 |
| JP | 62-267250 | 11/1987 |
| JP | 02-502723 | 8/1990 |
| JP | 05-339263 | 12/1993 |
| JP | 06-298746 | 10/1994 |
| JP | 08-134048 | 5/1996 |
| JP | 09-030960 | 2/1997 |
| JP | 2000-044533 | 2/2000 |
| JP | 2001-089472 | 4/2001 |
| NL | 7807819 | 1/1980 |
| SU | 1238732 A3 | 6/1986 |
| WF | WO 96/33993 A1 | 10/1996 |
| WO | WO 88/07858 A1 | 10/1988 |
| WO | WO 91/19698 A1 | 12/1991 |
| WO | WO 93/00094 A2 | 1/1993 |
| WO | WO 95/13274 A1 | 5/1995 |
| WO | WO 96/04271 A1 | 2/1996 |
| WO | WO 96/05194 A1 | 2/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02/074746 A1 | 9/2002 |
| WO | WO 03/000663 A1 | 1/2003 |
| WO | WO 03/027068 A2 | 4/2003 |
| WO | WO 03/062392 A2 | 7/2003 |
| WO | WO 03/086306 A2 | 10/2003 |
| WO | WO 2004/037788 A1 | 5/2004 |
| WO | WO 2005/003096 A1 | 1/2005 |
| WO | WO 2005/019179 A1 | 3/2005 |
| WO | WO 2005/042490 A1 | 5/2005 |
| WO | WO 2005/042491 A1 | 5/2005 |
| WO | WO 2006/013209 A2 | 2/2006 |
| WO | WO 2006/043710 A1 | 4/2006 |
| WO | WO 2006/069363 A2 | 6/2006 |
| WO | WO 2006/071740 A2 | 7/2006 |
| WO | WO 2007/120517 A2 | 10/2007 |
| WO | WO 2008/070111 A2 | 6/2008 |
| WO | WO 2009/111004 A1 | 9/2009 |

OTHER PUBLICATIONS

Barnes, Pharmacological Strategies for Relapse Prevention in Schizophrenia, Psychiatry, 3(10):37-40 (2004).

Bosch et al., "Studies on the Synthesis of Pentacyclic Strychnos Indole Alkaloids. Photocyclization of N-Chloroacetyl-1,2,3,4,5,6-hexahydro-1,5-methanoazocino [4,3-b] Indole Derivatives," Tetrahedron, 41(12):2557-66 (1985).

Bremner, "Seven Membered Rings," Institute for Biomolecular Science Dept. of Chemistry, University of Wollongong; "Progress in Heterocyclic Chemistry 13", Pergamon Press, Ch. 7:340-77 (2001).

Casy et al., "Some Arylalkylamino Analogs of Acyclic Analgetics", J Med Chem, (1968), 11(3):599-601.

Chang et al., "Dopamine Receptor Binding Properties of Some 2,3,4,5-Tetrahydro-1H-3-Benzazepine-7-ols With Non-Aromatic Substituents in the 5-Position", Bioorganic & Med. Chem. Letter, (1992) 2(5);399-402.

Chumpradit et al., "( )-7-chloro-8-hydroxyl-1-(4'-[125I]iodophenyl)-3-methyl-2,3,4,5-tetrahydro-1H-3-benzazepine: A Potential CNS D-1 Dopamine Receptor Imaging Agent," J. Med. Chem., 32:1431-5 (1989).

Clark et al., "1,9-alkano-bridged 2,3,4,5-tetrahydro-1H-3-benzzazepines with Affinity or the FJDK-Adrenoceptor and the 5-HT1A Receptor," J. Med. Chem., 33:633-41 (1990).

Deady, et al., "Synthesis of some tetrahydro-2- and 3-benzazepines, and of hexahydro-3-benzazocine," Journal of the Chemical Society, Perkins Transactions 1, 1973, pp. 782-783.

DeMarinis et al., "Development of an Affinity Ligand for Purification of KDAKLJ-Adrenoceptors from Human Platelet Membranes," J. Med. Chem., 27, 918-21 (1984).

Di Chiara et al., "Reward System and Addiction: What Dopamine Does and Doesn't Do", Current Opinion in Pharmacology 7:69-76 (2007).

Di Chiara, "Nucleus accumbens shell and core dopamine: differential role in behavior and addiction." (2002) Behavioural Brain Research, 137: 75-114.

Di Giovanni et al., "Serotonin/dopamine interaction—Focus on 5-HT2c receptor, a new target of psychotropic drugs," Indian Journal of Experimental Biology, vol. 40:1344-1352 (2002).

Di Matteo et al., "Role of 5-HT.sub.2C Receptors in the Control of Central Dopamine Function", Trends in Pharmacological Sciences 22(5):229-232 (2001).

Diagnostic and Statistical Manual of Mental Disorders, 4th edition, Text Revision,Washington, DC, American Psychiatric Association, 2000.

Dixit et al., "Gents Acting on Central Nervous System: Part XXIII—2-Substitutes 1,2,3,4,6,7,12,12a-Ochtahydropyrazino[2,l-b][3]benzazepines & 3-substituted 1,2,3,4,4a,5,6,11-Octahydropyrazin[l,2-b][2] benzazepines," CDRICommunication No. 1969, 893-97, (1974).

Draper et al., "Novel Stereoselective Syntheses of the Fused Benzazepine Dopamine D1 Antagonist (6aS, 13bR)-11-chloro-6,6a,7,8,9, 13b-hexahydro-7-methyl-5H-benzo[d]naphth[2,1-b]axepin-12-ol (Sch 39166):1. Aziridinium Salt Based Syntheses," Organic Process Research & Development 2(3j:175-85 (1998).

Flannery-Schroeder, "Reducing Anxiety to Prevent Depression," Am. J. Prey. Med. 31(6S1):S136-S142 (2006).

Fuchs et al., "Total Synthesis of (+/−)-Lennoxamine and (+/−)-Aphanorphine by Intramolecular Electrophilic Aromatic Substitution Reactions of 2-Amidoacroleins," Organic Letters, 2001, pp. 3923-3925, 3(24).

Gallant et al., "U-22,394A: a controlled evaluation in chronic schizophrenic patients," Current Therapy Research, 9(11):579-81(1967).

Gardent et al., "Sur quelques de l'amino-2-bromo-4 1H benzazepine-3 et de ses derives," Bull Soc. Chim. France (1968) 2:600-605.

(56) References Cited

OTHER PUBLICATIONS

Gerace et al., "Predictors of Weight Increases over 7 Years in Fire Fighters and Paramedics," Preventive Medicine, 25:593-600 (1996).
Gerritz et al., "Two General Routes to 1,4-disubstituted-2,3,4,5-tetrahydro-1H-3-benzazepines," Organic Letters, 2(25):4099-102 (2000).
Gobert et al., "Serotonin2c Receptors Tonically Suppress the Activity of Mesocortical Dopaminergic and Adrenergic, But Not Serotonergic, Pathways: A Combined Dialysis and Electrophysiological Analysis in the Rat," Synapse, 36:205-221 (2000).
Gombar et al., "Pharmacokinetics of a series of 6-chloro-2, 3, 4, 5-tetrahydro-3-substituted-1H-3-benzazepines in rats," Drug Metab. Disposition (1988) 16:367-372.
Greene et al., Protective Groups in Organic Synthesis, 2.sup.nd Ed., Wiley and Sons, NY 1991.
Griesser, "Polymorphism in the Pharmaceutical Industry," ed. Rolf Hilfiker, Wiley,VCH Verlag GmbH & Co.: pp. 211-233 (2006).
Halford et al., "Serotonergic Drugs: Effects on Appetite Expression and Use for the Treatment of Obesity," Drugs, 67(1): 27-55 (2007).
Hasan et al., "Syntheses of N-chloroacyl-beta-phenylethylamine Derivatives," Indian J. Chem., 9:1022-4 (1971).
Hassine-Coniac et al., "Preparation et properietes d'aldehydes dans la serie de la benzazapine-3," Bull Soc. Chim. Fance (1971) 11:3985-3992.
Hazerbroucq "Acces a des I-H, tetrahydro-2, 3, 4, 5 benzazepines-3 one-1 et a des hexahydro imidazo isoguinoleines," Ann. Chim. (1966) pp. 221-254.
Helferich et al., "Uber Derivate Einger Chinolincarbonsauren," J. Fur Praktische Chemie, vol. 33, 1966, 39-48.
Hester et al., "Azepinoindoles. I. Hexahyclroazepino[4,5-b)indoles," J. Med. Chem, 11(1):101-106 (1968).
Heys et al., "A New Entry into C7-Oxygenated Tetrahydro-1H-3-benzazepines:Efficient Labeling with Carbon-14 in the Benzo Ring," J. Org. Chem., 54(19):4702-6 (1989).
Higgins et al., "Serotonin and drug reward: focus on 5-HT2c receptors," European Journal of Pharmacology, 480:151-162, (2003).
Hitzig, "Combined Serotonin and Dopamine Indirect Agonistscorrectalcohol Craving and Alcohol-Associated Neuroses," Journal of Substance Abuse Treatment, 11(5):489-90 (1994).
Im et al., "Positive Allosteric Modulator of the Human 5-HT2C Receptor," MolecularPharmacology, 64: 78-84 (2003).
Jenck et al., "Antiaversive effects of 5-HT2c receptor agonists and fluoxetine in a model of panic-like anxiety in rats," European Neuropsychopharmacology, 8:161(1998).
Jensen et al., "Potential Role of New Therapies in Modifying Cardiovascular Risk in Overweight Patients with Metabolic Risk Facts", Obesity 14 (Suppl. 3):143S-149S (2006).
Kaiser et al., "6-(Phenylthio)-substituted 2,3,4,5-tetrahydro-1H-3-benzazepines, a Novel Class of Dopamine Receptor Antagoists and Neuroleptics," J. Med. Chem., 23(9):975-6 (1980).
Karasu et al., (2000) Practice Guideline for the Treatment of Patients with MajorDepressive Disorder.
Klohr et al., "An Intramolecular Photocyclization to Form the Azepino[3,4,5-cd]Indole System," Synthetic Communications 18(7):671-4 (1988).
Koplan et al., "Preventing Childhood Obesity: Health in the Balance, Executive Summary", http://www.nap.edu/catalog/11015.html, 41 pages (2005).
Kuenburg et al., "Development of a Pilot Scale Process for the Anti-Alzheimer Drug (−)-Galantahmine Using Large-Scale Phenolic Oxidative Coupling and Crystallisation-Induced Chiral Conversion," Organic Process Research & Development, 3(6):425-31 (1999)..
Lacivita et al., "Selective Agents for Serotonin2C (5-HTC2C) Receptor," Current Topics in Medicinal Chemistry, vol. 6:pp. 1927-1970 (2006).
Ladd et al., "Synthesis and Dopaminergic Binding of 2-Aryldopamine Analogues: Phenethylamines, 3-Benzazepines, and 9-(Aminomethyl)flourenes", J. Med, Chem., (1986) 29(10):1904-1912.
Lam et al., (1999) (eds) Canadian Consensus Guidelines for the Treatment ofSeasonal Affective Disorder, Clinical & Academic Publishing, Vancouver, BC, Canada.
Lennon et al., "Azabenzocycloheptenones. Part XVIII. Amines and amino-ketones of the tetrahydro-3-benzazepine-1-one series," J. Chem. Soc. Perkin Transacts. (1975) 7:622-626.
Lin et al., "Benzindene Prostaglandins. Synthesis of Optically Pure 15-Deoxy-U-68,215 and its Enantiomer via a Modified Intramolecular Wadsworth-Emmons-Witting Reaction," J. Org. Chem., 52(25):5594-601 (1987).
MacDonald et al., "Design and synthesis of trans-3-(2-(4-((3-(3-(5-methyl-1,2,4-oxadiazolyl))-phenyl)carboxamido)cyc- 1 ohexyl)ethyl)-7-methylsulfonyl-2,3,4,5-tetrahydro-1H-3-benzazepine (SB-414796): A Potent and selective dopamine D3 Receptor Antagonist," J. Med. Chem., 2003, 4952-4964, vol. 46, American Chemical Society.
Moline et al., "Postpartum Depression: A Guide for Patients and Families," ExpertConsensus Guidelines Series—Treatment of Depression in Woman 2001, Mar. 2001: 112-113.
Muller et al., "Intracellular 5-HT2C-receptor Dephosphorylation: A New Target for Treating Drug Addiction," Trends in Pharmacological Sciences 27(9):455-58 (2006).
Nagase et al., "An anhydrous polymorphic form of trehalose, " Carbohydrate Research 337(2),167-173 (2002) (Abstract).
Nagle et al., "Efficient Synthesis of beta-amino Bromides," Tetrahedron Letters, 41:3011-4 (2000).
Nair et al., "Prepartion of 2,3,4,5-tetrahydro-3,1H-benzazepine-2-one," Indian J. Chem., 5:169-70. (1967).
Navarro-Vazquez et al., "A study of aryl radical cyclization in enaminone esters," J. Org. Chem. 67:3213-20 (2002).
Neumeyer et al., "Development of a High Affinity and Stereoselective Photoaffinity Label for the D-1 Dopamine Receptor: Synthesis and Resolution of 7-[125I]Iodo-8-hydroxy-3-methyl-1-(4'-azidophenyl)-2,3,4,5-tetrahydro-1H-3-benzazepine," J. Med. Chem., 33(20):521-6 (1990).
Niendam et al., "Neurocognitive Performance and Functional Disablility in the Psychosis Prodrome," Schizophrenia Research, 84:100-111 (2006).
Okuno et al., "Photocyclization of N-chloroacetyl-2,5-dimethoxyphenethylamine Synthesis of Pyrroloindoles," Chem. Pharm. Bull., 23(11):2584-90 (1975).
Orito et al., Hokkaido Daigaku Kogakubu Kenkyu Hokoku (1979), (96), 41-44.
Orito et al., "Alkylation of 1,2,4,5-Tetrahydro-3-methyl-3H-3-Benzazepin-2-One with Sodium Hydride and Alkyl Halide," Tetrahedron 36:1017-1021 (1980) Permagon Press Ltd.
Orito et al., "Total Synthesis of Pseudo Type of Protopine Alkaloids," Heterocycles 14(1), 11-14 (1980).
Orito et al., "Synthetic studies of heterocyclic compounds I. Alkylation and acylation of 1,2,4,5-tetrahydro-3-methyl-3H-3-benzazepin-2-one," CASREACT, 1979, 93:7990.
Pauvert et al., "Silver Nitrate-Promoted Ring Enlargement of 1-Tribromomethyl-1,2-dihydro- and 1-Tribromomethyl-1,2,3,4-tetrahydro-isoquinoline Derivatives: Application to the Synthesis of the Anti-anginal Zatebradine," Tetrahedron Letters, 44:4203-6 (2003), Pergamon Press Ltd.
Pawan et al., "Preliminary study on the effects of fenfluramine derivative, 'S992' inman," British Jornal of Pharmacology, 41(2): 416P-417P (1971) (CAPLUS abstract).
Pecherer et al., "A Novel Synthesis of Aromatic Methoxy and Methylenedioxy Substituted 2,3,4,5-tetrahydro-1H-3-benazaepines," J. Het. Chem., 9:609-16 (1972).
Pecherer et al., "The Synthesis of Some 7- and 7,8-substituted 2,3,4,5-tetrahydro-1H-3-benzazepines," J. Heterocyclic Chemistry 8(5):779-783 (1971).
Perry et al., "Prospective study of risk factors for development on non-insulin dependent diabetes in middle aged British men," BMJ (1995) 310:560-564.
Pfeiffer et al., "Dopaminergic Activity of Substituted 6-chloro-1-phenyl-2,3,4,5-tetrahydro-1H-3-benzazepines," J. Med. Chem., 25(4):352-8 (1982).
Piesla et al., (2001), Schizophrenia Research, 49:95.

(56) References Cited

OTHER PUBLICATIONS

Porras et al., "5-HT2a and 5-HT2c/2b Receptor Subtypes Modulate Dopamine ReleaseInduced in Vivo by Amphetamine and Morphine in Both the Rat Nucleus Accumbensand Striatum," Neuropsychopharmacology, 26: 311-324 (2002).

Prous Science Integrity entry 156186, 2007.

Prous Science Integrity entry 354056, 2007.

Remington's Pharmaceutical Sciences, 17th ed., Mack Publishing Company, Easton Pa.: 1418 (1985).

Rothman, "Treatment of alcohol and cocaine addiction by the combination of pemoline and fenfluramine: a preliminary case series." (1995) Journal of Substance Abuse Treatment, 12(6): 449-453.

Schaffner et al., "Preventing Severe Mental Illnesses—New Prospects and Ethical Challenges," Schizophrenia Research, 51:3-15 (2001).

Schlademan et al., "Synthesis of oxo- and 1-hydroxy-azobenzocycloalkanes," J. Chem. Soc. Perkin Transacts. (1972) 2:213-215.

Smith et al., "Discovery and SAR of New Benzazepines as Potent and Selective 5HT2c Receptor Agonists for the Treatment of Obesity," Bioorganic & Medicinal Chemistry Letters, 15(5):1467-1470 (2005).

Smith et al., "Discovery and Structure—Activity Relationship of (1R)-8-Chloro-2,3,4,5-tetrahydro-I-methyl-1H-3-benzazepine (Lorcaserin), a Selective Serotonin 5-HT2c Receptor Agonist for the Treatment of Obesity," [retrieved on Dec. 21, 2007]. Retrieved from the Internet. <URL:http://pubs.acs.orgijournals/jmcmar/index.html>.

Tietze et al., "Efficient Synthesis of 2,3,4,5-tetrahydro-1H-3-benzazepines by intermolecular heck Reaction," Institut fur Organische Chemie der Universtat Gottingen, Tammannstrasse 2, D-3400 Gottingen, Germany.

Tsuang et al., Towards the Prevention of Schizophrenia, B245 Biol. Psychiatry, 48:349-356 (2000).

Van Oekelen et al., "5-HT2A and 5-HT2C receptors and their atypical regulation properties," Life Sciences, vol. 72:2429-2449 (2003).

Vanderlaan et al., "Synthesis and Oxidative Coupling of ( )-3-oxoreticuline," J. Org. Chem., 50(6):743-7 (1985).

Vink et al., "Risk Factors for Anxiety and Depression in the Elderly: A Review", J. Affect. Disord., doi:10.1016/j.jad.2007.06.005, 16 pages (2007).

Weinstock et al., "Separation of Potent Central and Renal Dopamine Agonist Activity in Substituted 6-chloro-2,3,4,5-tetrahydro-7,8-dihydroxy-1-phenyl-1H-3-benzazepines," J. Med. Chem., 23(9):973-5 (1980).

Wilk, (1988) Pol. J. Chem. 62:895.

Williams, Chemistry Demystified 123 (2003).

Wise, "Addiction becomes a brain disease", (2000) Neuron, 26: 27-33.

Wisner et al., "Clinical practice. Postpartum depression." (2002) N. Engl. J. Med., 347(3): 194-199.

Yoshinaga et al., "Prevention of Mildly Overweight Children from Development of More Overweight Condition," Preventon Medicine, 38:172-174 (2004).

Zhang et al., Chem. Lett. 12:2271 (1994).

\* cited by examiner

PROCESSES FOR PREPARING 3-BENZAZEPINES

CROSS-REFERENCE TO RELATED APPLICATIONS

This is a continuation application of U.S. patent application Ser. No. 10/560,953, filed Apr. 26, 2007 now U.S. Pat. No. 8,367,657, which is a 35 USC 371 National Stage Application of PCT/US04/19279, filed Jun. 16, 2004, and claims priority to U.S. Patent Application Nos. 60/479,280, filed Jun. 17, 2003, and 60/512,967, filed Oct. 21, 2003.

FIELD OF THE INVENTION

The present invention generally relates to processes and intermediates for the preparation of 3-benzazepines and salts thereof which can be useful as serotonin (5-HT) receptor agonists for the treatment of, for example, central nervous system disorders such as obesity.

BACKGROUND OF THE INVENTION

Serotonin (5-HT) neurotransmission plays an important role in numerous physiological processes both in health and in psychiatric disorders. For example, 5-HT has been implicated in the regulation of feeding behavior. 5-HT is believed to work by inducing a feeling of fullness or satiety so eating stops earlier and fewer calories are consumed. It has been shown that a stimulatory action of 5-HT on the $5HT_{2C}$ receptor plays an important role in the control of eating and in the anti-obesity effect of d-fenfluramine. As the $5\text{-}HT_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective $5\text{-}HT_{2C}$ receptor agonist can be a more effective and safe anti-obesity agent. Also, $5\text{-}HT_{2C}$ knockout mice are overweight with cognitive impairment and susceptibility to seizure. Thus, the $5HT_{2C}$ receptor is recognized as a well-accepted receptor target for the treatment of obesity, psychiatric, and other disorders.

3-Benzazepines have been found to be agonists of the $5HT_{2C}$ receptor and show effectiveness at reducing obesity in animal models (see, e.g., U.S. Ser. No. 60/479,280 and U.S. Ser. No. 10/410,991, each of which is incorporated herein by reference in its entirety). Numerous synthetic routes to 3-benzazepines have been reported and typically involve a phenyl-containing starting material upon which is built an amine- or amide-containing chain that is capable of cyclizing to form the fused 7-member ring of the benzazepine core. Syntheses of 3-benzazepines and intermediates thereof are reported in U.S. Ser. No. 60/479,280 and U.S. Ser. No. 10/410,991 as well as Nair et al., *Indian J. Chem.*, 1967, 5, 169; Orito et al., *Tetrahedron*, 1980, 36, 1017; Wu et al., *Organic Process Research and Development*, 1997, 1, 359; Draper et al., *Organic Process Research and Development*, 1998, 2, 175; Draper et al., *Organic Process Research and Development*, 1998, 2, 186; Kuenburg et al., *Organic Process Research and Development*, 1999, 3, 425; Baindur et al., *J. Med. Chem.*, 1992, 35(1), 67; Neumeyer et al., *J. Med. Chem.*, 1990, 33, 521; Clark et al., *J. Med. Chem.*, 1990, 33, 633; Pfeiffer et al., *J. Med. Chem.*, 1982, 25, 352; Weinstock et al., *J. Med. Chem.*, 1980, 23(9), 973; Weinstock et al., *J. Med. Chem.*, 1980, 23(9), 975; Chumpradit et al., *J. Med. Chem.*, 1989, 32, 1431; Heys et al., *J. Org. Chem.*, 1989, 54, 4702; Bremner et al., *Progress in Heterocyclic Chemistry*, 2001, 13, 340; Hasan et al., *Indian J. Chem.*, 1971, 9(9), 1022; Nagle et al., *Tetrahedron Letters*, 2000, 41, 3011; Robert, et al. *J. Org. Chem.*, 1987, 52, 5594); and Deady et al., *J. Chem. Soc., Perkin Trans. I*, 1973, 782.

Other routes to 3-benzazepines and related compounds are reported in Ladd et al., *J. Med. Chem.*, 1986, 29, 1904; EP 204349; EP 285 919; CH 500194: *Tetrahedron Letters*, 1986, 27, 2023; *Ger. Offen.*, 3418270, 21 Nov. 1985; *J. Org. Chem.*, 1985, 50, 743; U.S. Pat. Nos. 4,957,914 and 5,015,639; *Synthetic Commun.*, 1988, 18, 671; *Tetrahedron*, 1985, 41, 2557; *Hokkaido Daigaku Kogakubu Kenkyu Hokoku*, 1979, 96, 41-4; *Chemical & Pharmaceutical Bulletin*, 1975, 23, 2584; *J. Am. Chem. Soc.*, 1970, 92, 5686; *J. Am. Chem. Soc.*, 1968, 90, 6522; *J. Am. Chem. Soc.*, 1968, 90, 776; *J. Am. Chem. Soc.*, 1967, 89, 1039; and Chang et al., *Bioorg. Med. Chem. Letters*, 1992, 2, 399

In view of the growing demand for compounds for the treatment of disorders related to the $5\text{-}HT_{2C}$ receptor, new and more efficient routes to 3-benzazepines are needed. The processes and compounds described herein help meet these and other needs.

SUMMARY OF THE INVENTION

The processes and intermediates of the present invention are useful in the preparation of therapeutic agents for the treatment or prophylaxis of 5-HT mediated disorders such as obesity and other central nervous system diseases.

The present invention provides, inter alia, a process for preparing a compound of Formula I:

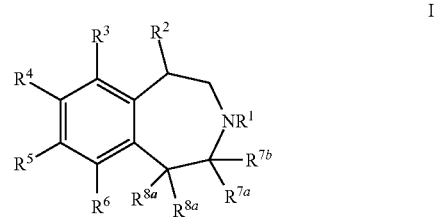

or salt form thereof,
wherein:

$R^1$ is $R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising reacting a compound of Formula II:

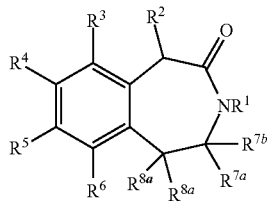

II with a reducing agent optionally in the presence of a Lewis acid for a time and under conditions suitable for forming said compound of Formula I or salt form thereof.

The present invention further provides a process for preparing a compound of Formula II or salt form thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising reacting a compound of Formula III:

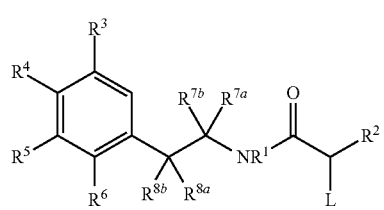

III or salt thereof, wherein:

L is halo, hydroxy, $C_1$-$C_8$ alkoxy, $C_1$-$C_8$ thioalkoxy, $C_1$-$C_8$ acyloxy, —$OSO_2R$, or —$OSi(R')_3$;

R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy;

R' is $C_1$-$C_8$ alkyl;

with a cyclizing reagent for a time and under conditions suitable for forming said compound of Formula II or salt form thereof.

The present invention further provides a process for preparing a compound of Formula I or salt form thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising:
(a) reacting a compound of Formula III:

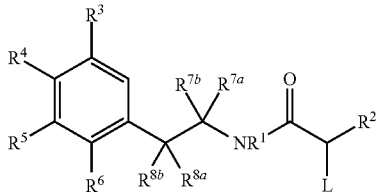

III or salt form thereof,
wherein:
L is halo, hydroxy, $C_1$-$C_8$ alkoxy, $C_1$-$C_8$ thioalkoxy, $C_1$-$C_8$ acyloxy, —$OSO_2R$, or —$OSi(R')_3$;
R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and
R' is $C_1$-$C_8$ alkyl;
with a cyclizing reagent for a time and under conditions suitable for forming a compound of Formula II or salt form thereof; and
(b) reacting said compound of Formula II or salt form thereof with a reducing agent optionally in the presence of a Lewis acid for a time and under conditions suitable for forming said compound of Formula I or salt form thereof.

The present invention further provides a process for preparing a compound of Formula I or salt form thereof,
wherein:
$R^1$ is H or $C_1$-$C_8$ alkyl;
$R^2$ is $C_1$-$C_8$ alkyl, —$CH_2$—O—($C_1$-$C_8$ alkyl), $C(O)O$—($C_1$-$C_8$ alkyl), —$C(O)NH$—($C_1$-$C_8$ alkyl), OH, $C_1$-$C_4$ haloalkyl, or $CH_2OH$;
$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, $C(O)$-alkyl, $C(O)O$-alkyl, $C(O)NH$-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;
$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, $C(O)$-alkyl, $C(O)O$-alkyl, $C(O)NH$-alkyl, or hydroxyalkyl, or $R^{7a}$ and $R^{7b}$ together with the carbon atom to which they are attached form a $C_3$-$C_7$ cycloalkyl group;
$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, $C(O)$-alkyl, $C(O)O$-alkyl, $C(O)NH$-alkyl, or hydroxyalkyl, or $R^{8a}$ and $R^{8b}$ together with the carbon atom to which they are attached form a $C_3$-$C_7$ cycloalkyl group;
$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and
$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising:
(a) reacting a compound of Formula IV:

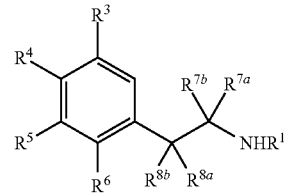

IV or salt form thereof, with a compound of Formula:

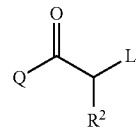

wherein:
L is halo, hydroxy, $C_1$-$C_8$ alkoxy, $C_1$-$C_8$ thioalkoxy, $C_1$-$C_8$ acyloxy, —$OSO_2R$, or —$OSi(R')_3$;
R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy;
R' is $C_1$-$C_8$ alkyl; and
Q is a leaving group,
for a time and under conditions suitable for forming a compound of Formula III
or salt form thereof;
(b) reacting said compound of Formula III or salt form thereof,
with a cyclizing reagent for a time and under conditions suitable for forming a compound of Formula II or salt form thereof; and
(c) reacting said compound of Formula II with a reducing agent optionally in the presence of a Lewis acid for a time and under conditions suitable for forming said compound of Formula I or salt form thereof.

The present invention further provides a process for preparing a compound of Formula I or salt form thereof,
wherein:
$R^1$ is H or $C_1$-$C_8$ alkyl;
$R^2$ is $C_1$-$C_8$ alkyl, —$CH_2$—O—($C_1$-$C_8$ alkyl), $C(O)O$—($C_1$-$C_8$ alkyl), —$C(O)NH$—($C_1$-$C_8$ alkyl), OH, $C_1$-$C_4$ haloalkyl, or $CH_2OH$;
$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, $C(O)$-alkyl, $C(O)O$-alkyl, $C(O)NH$-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;
$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, $C(O)$-alkyl, $C(O)O$-alkyl, $C(O)NH$-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising reacting a compound of Formula IIIa:

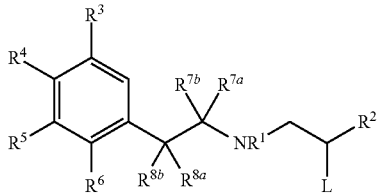

IIIa wherein:

L is halo, hydroxy, $C_1$-$C_8$ alkoxy, $C_1$-$C_8$ thioalkoxy, $C_1$-$C_8$ acyloxy, —OSO$_2$R, or —OSi(R')$_3$;

R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and R' is $C_1$-$C_8$ alkyl;

with a cyclizing reagent for a time and under conditions suitable for forming said compound of Formula I.

The present invention further provides a process for preparing a compound of Formula IIIa or salt form thereof, wherein:

$R^1$ is H or $C_1$-$C_8$ alkyl;

$R^2$ is $C_1$-$C_8$ alkyl, —CH$_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or CH$_2$OH;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, OR$^9$, SR$^9$, alkoxyalkyl, C(O)-alkyl, C(O)O-alkyl, C(O)NH-alkyl, hydroxyalkyl, NR$^{10}$R$^{11}$, CN, NO$_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

L is halo, hydroxy, $C_1$-$C_8$ alkoxy, $C_1$-$C_8$ thioalkoxy $C_1$-$C_8$ acyloxy, —OSO$_2$R, or —OSi(R')$_3$;

R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and R' is $C_1$-$C_8$ alkyl;

comprising reacting a compound of Formula III:

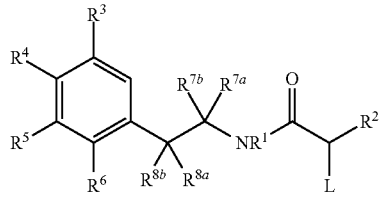

III with a reducing agent optionally in the presence of a Lewis acid for a time and under conditions suitable for forming said compound of Formula IIIa.

The present invention further provides a process for preparing a compound of Formula I or salt form thereof, wherein:

$R^1$ is H or $C_1$-$C_8$ alkyl;

$R^2$ is $C_1$-$C_8$ alkyl, —CH$_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or CH$_2$OH;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, OR$^9$, SR$^9$, alkoxyalkyl, C(O)-alkyl, C(O)O-alkyl, C(O)NH-alkyl, hydroxyalkyl, NR$^{10}$R$^{11}$, CN, NO$_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising
a) reacting a compound of Formula III
wherein:
L is halo, hydroxy, $C_1$-$C_8$ alkoxy, $C_1$-$C_8$ thioalkoxy, $C_1$-$C_8$ acyloxy, —$OSO_2R$, or —$OSi(R')_3$;
R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and
R' is $C_1$-$C_8$ alkyl;
with a reducing agent optionally in the presence of a Lewis acid for a time and under conditions suitable for forming a compound of Formula IIIa;
and
b) reacting said compound of Formula IIIa with a cyclizing reagent for a time and under conditions suitable for forming said compound of Formula I.

The present invention further provides a process for preparing a compound of Formula I or salt form thereof,
wherein:
$R^1$ is H or $C_1$-$C_8$ alkyl;
$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;
$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;
$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;
$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;
$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;
$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;
comprising:
(a) reacting a compound of Formula IV
or salt form thereof, with a compound of Formula:

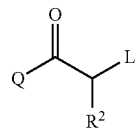

wherein:
L is halo, hydroxy, $C_1$-$C_8$ alkoxy, $C_1$-$C_8$ thioalkoxy, $C_1$-$C_8$ acyloxy, —$OSO_2R$, or —$OSi(R')_3$;
R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy;
R' is $C_1$-$C_8$ alkyl; and
Q is a leaving group,
for a time and under conditions suitable for forming a compound of Formula III or salt form thereof;
(b) reacting said compound of Formula III with a reducing agent optionally in the presence of a Lewis acid for a time and under conditions suitable for forming a compound of Formula IIIa; and
(c) reacting said compound of Formula IIIa with a cyclizing reagent for a time and under conditions suitable for forming said compound of Formula I.

The present invention further provides a method of resolving a mixture of compounds of Formulas Ia and Ib:

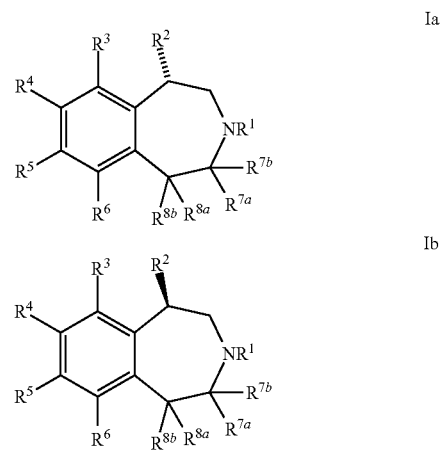

wherein:
$R^1$ is H or $C_1$-$C_8$ alkyl;
$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;
$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;
$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;
$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising:

contacting said mixture of compounds with a chiral resolving acid to form chiral resolving acid salts of said compounds, wherein said chiral resolving acid comprises substantially one stereoisomer; and precipitating said chiral resolving acid salts of said compounds, wherein the resulting precipitate is enriched in the chiral resolving acid salt of one of said compounds of Formula Ia or Ib.

The present invention further provides a compound of Formula II or IIIa or salt form thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

L is halo, hydroxy, $C_1$-$C_8$ alkoxy, $C_1$-$C_8$ thioalkoxy, $C_1$-$C_8$ acyloxy, —$OSO_2R$, or —$OSi(R')_3$;

R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and R' is $C_1$-$C_8$ alkyl.

The present invention further provides a chiral resolving acid salt of a compound of Formula Ia or Ib wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring.

The present invention further provides a process for preparing a compound of Formula V:

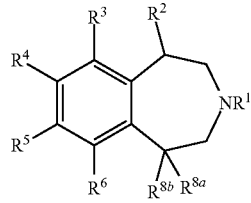

or salt thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), or $C_1$-$C_4$ haloalkyl;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising reacting a compound of Formula IX:

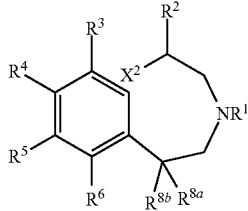

IX or salt thereof, wherein $X^2$ is halo or $SO_2R''$ and $R''$ is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy, with a cyclizing reagent for a time and under conditions suitable for forming said compound of Formula V.

The present invention further provides a process for preparing a compound of Formula X:

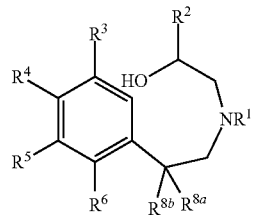

X or salt thereof,
wherein:
$R^1$ is H or $C_1$-$C_8$ alkyl;
$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), or $C_1$-$C_4$ haloalkyl;
$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising reacting a compound of Formula XI:

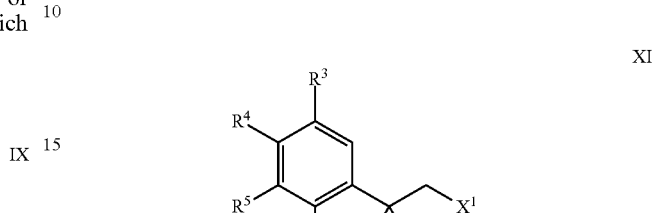

XI wherein $X^1$ is a leaving group,
with a compound of Formula:

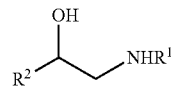

for a time and under conditions suitable for forming said compound of Formula X.

The present invention further provides a process for preparing a compound of Formula V or salt thereof,
wherein:
$R^1$ is H or $C_1$-$C_8$ alkyl;
$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), or $C_1$-$C_4$ haloalkyl;
$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising:
a) reacting a compound of Formula X or salt thereof; with a halogenating/sulfonating reagent for a time and under conditions suitable for forming a compound of Formula IX or salt thereof;

wherein $X^2$ is halo or $SO_2R''$ and $R''$ is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and b) reacting said compound of Formula IX with a cyclizing reagent for a time and under conditions suitable for forming said compound of Formula V.

The present invention further provides a process for preparing a compound of Formula V or salt thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), or $C_1$-$C_4$ haloalkyl;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising:

a) reacting a compound of Formula XI:

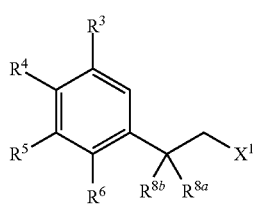

XI wherein $X^1$ is a leaving group, with a compound of Formula:

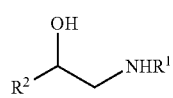

or salt thereof, for a time and under conditions suitable for forming a compound of Formula X or salt thereof;

b) reacting said compound of Formula X with a halogenating/sulfonating reagent for a time and under conditions suitable for forming a compound of Formula IX or salt thereof;

wherein $X^2$ is halo or $SO_2R''$ and $R''$ is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and c) reacting said compound of Formula IX with a cyclizing reagent for a time and under conditions suitable for forming said compound of Formula V.

The present invention further provides a process for preparing a compound of Formula V or salt thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), or $C_1$-$C_4$ haloalkyl;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising:

a) reacting a compound of Formula XII:

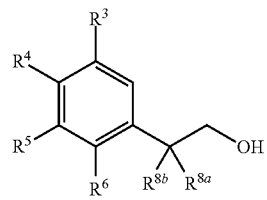

XII with a halogenating/sulfonating reagent for a time and under conditions suitable for forming a compound of Formula XI wherein $X^1$ is a leaving group;

b) reacting said compound of Formula XI with a compound of Formula:

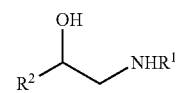

or salt thereof, for a time and under conditions suitable for forming a compound of Formula X or salt thereof;

c) reacting said compound of Formula X with a further halogenating/sulfonating reagent for a time and under conditions suitable for forming a compound of Formula IX or salt thereof;

wherein $X^2$ is halo or $SO_2R''$ and $R''$ is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and d) reacting said compound of Formula IX with a cyclizing reagent for a time and under conditions suitable for forming said compound of Formula V.

The present invention further provides a compound of Formula IX or X
or salt form thereof,
wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), or $C_1$-$C_4$ haloalkyl;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring; and $X^2$ is halo or $SO_2R''$; and $R''$ is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy.

The present invention further provides a method of resolving a mixture of compounds of Formula Va and Vb:

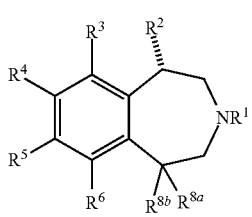

Va

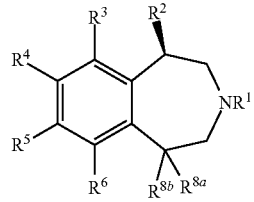

Vb wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

comprising:

contacting said mixture of compounds with a chiral resolving acid to form chiral resolving acid salts of said compounds, wherein said chiral resolving acid comprises substantially one stereoisomer, and precipitating said chiral resolving acid salts of said compounds, wherein the resulting precipitate is enriched in the chiral resolving acid salt of one of said compounds of Formula Va or Vb.

The present invention further provides a chiral resolving acid salt of a compound of Formula Va or Vb
wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring.

DETAILED DESCRIPTION OF EMBODIMENTS OF THE INVENTION

The processes and intermediates of the present invention are useful in the preparation of therapeutic agents for the treatment or prophylaxis of 5-HT mediated disorders such as obesity and other central nervous system diseases.

Example processes and intermediates of the present invention are provided below in Scheme I, wherein constituent members for the compounds depicted therein are defined hereinbelow. The symbol "*" designates optionally chiral centers that can be substantially retained or inverted over the course of the depicted reactions.

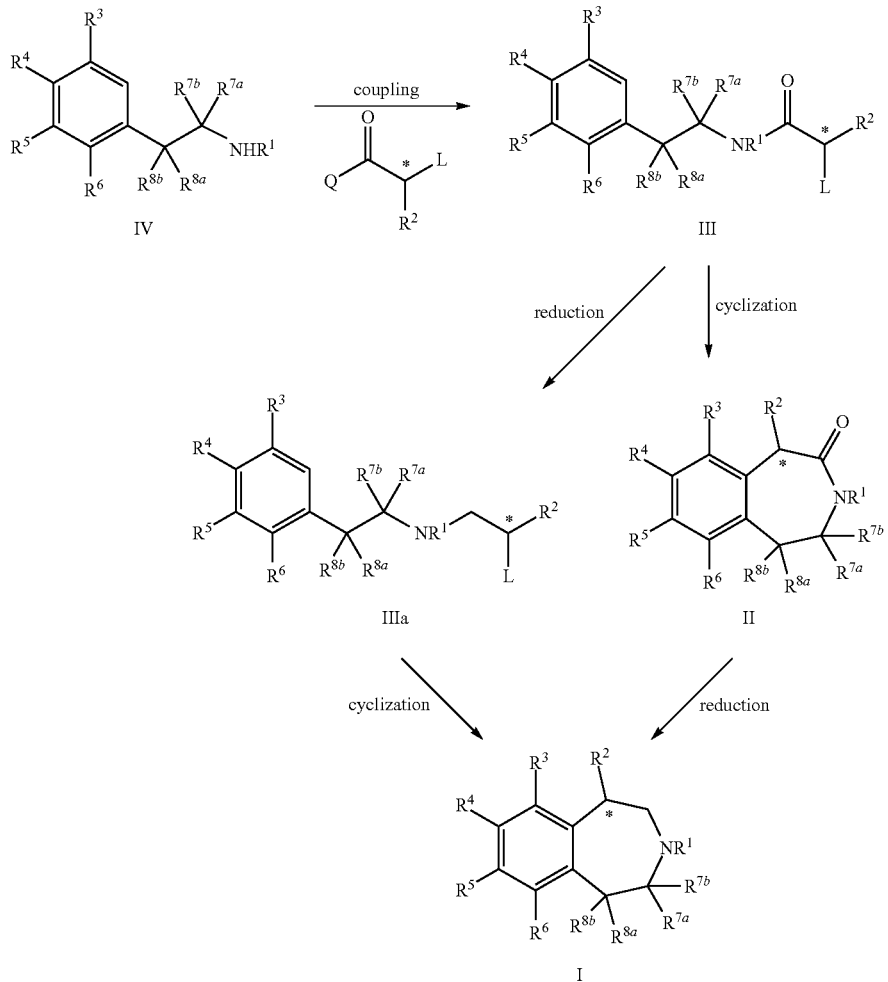

Scheme I

In a first aspect of the invention are provided processes, such as are exemplified by Scheme I, that involve compounds of Formulas I, Ia, Ib, II, III, IIIa, and IV, or salt forms thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl;

$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

L is halo, hydroxy, $C_1$-$C_8$ alkoxy, $C_1$-$C_8$ thioalkoxy, $C_1$-$C_8$ acyloxy, —OSO$_2$R, or —OSi(R')$_3$;

R is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy; and R' is $C_1$-$C_8$ alkyl.

In some embodiments:

$R^2$ is $C_1$-$C_8$ alkyl, —CH$_2$—O—($C_1$-$C_8$ alkyl), C(O)O—($C_1$-$C_8$ alkyl), —C(O)NH—($C_1$-$C_8$ alkyl), OH, or CH$_2$OH;

$R^3$ and $R^6$ are each H;

$R^4$ and $R^5$ are each, independently, H, halo, $C_1$-$C_8$ haloalkyl, hydroxy, OR$^9$, SR$^9$, alkoxyalkyl, NHR$^{10}$, NR$^{10}$R$^{11}$, aryl, or heteroaryl, wherein said aryl can be substituted with up to two substituents selected from $C_1$-$C_8$ alkyl, halo, $C_1$-$C_8$ haloalkyl, and alkoxy, and said heteroaryl can be optionally substituted with up to two substituents selected from halogen and $C_1$-$C_8$ alkyl; or $R^4$ and $R^5$ together with the atoms to which they are attached form a 5- or 6-member heterocyclic ring having one O atom;

$R^{7a}$ is H;

$R^{7b}$ is H or $C_1$-$C_8$ alkyl;

$R^{8a}$ and $R^{8b}$ are each H; and $R^{10}$ and $R^{11}$ are each, independently, $C_1$-$C_8$ alkyl, $C_1$-$C_8$ alkenyl, $C_1$-$C_8$ haloalkyl, aryl, heteroaryl, aralkyl, heteroarylalkyl, or allyl.

In some embodiments, (A) if $R^2$ is methyl and $R^4$ is H, then $R^5$ is not thiazole, substituted thiazole or a thiazole derivative;

In some embodiments, (B) if $R^{7a}$ is H and $R^{7b}$ is other than H, then neither $R^4$ nor $R^5$ can be H;

In some embodiments, (C) if $R^1$ and $R^2$ are methyl, and $R^5$ is H then $R^4$ is not NHR$^{10}$ or NR$^{10}$R$^{11}$;

In some embodiments, (D) if $R^1$ and $R^2$ are methyl and $R^5$ is H, then $R^4$ is not imidazolyl, substituted imidazolyl, or an imidazole derivative;

In some embodiments, (E) if $R^1$ is H or CH$_3$, and $R^2$ is CH$_3$ or OH, then $R^3$, $R^4$, $R^5$, and $R^6$ cannot all be H.

In some embodiments, (F) if $R^1$ is H and $R^2$ is isopropyl or OH, then $R^4$ and $R^5$ cannot both be OCH$_3$ or OH.

In some embodiments, (G) if $R^1$ is CH$_3$ and $R^2$ is n-propyl, then $R^4$ cannot be OH, $R^5$ cannot Cl, and $R^3$ and $R^6$ cannot both be H.

In further embodiments, $R^1$ is H.

In further embodiments, $R^1$ is $C_1$-$C_8$ alkyl.

In further embodiments, $R^2$ is methyl, ethyl, n-propyl, or isopropyl.

In further embodiments, $R^2$ is methyl.

In further embodiments, $R^4$ is Cl, Br, haloalkyl, CF$_3$, thiophenyl, furanyl, pyrrolyl, pyrazolyl, or imidazolyl.

In further embodiments, $R^4$ is Cl.

In further embodiments, $R^5$ is methoxy, ethoxy, n-propoxy, isopropoxy, allyloxy, thiophenyl, furanyl, pyrrolyl, pyrazolyl, imidazolyl, or phenyl, wherein said imidazolyl is optionally substituted by one or more halo or methyl and said phenyl is optionally substituted with up to two substituents selected from $C_1$-$C_8$ alkyl, $C_1$-$C_8$ haloalkyl, halo, and alkoxy.

In further embodiments, $R^5$ is H.

In some embodiments:

$R^2$ is $C_1$-$C_4$ alkyl, —CH$_2$—O—($C_1$-$C_4$ alkyl), $C_1$-$C_4$ haloalkyl, or CH$_2$OH;

$R^3$, $R^4$, $R^5$, and $R^6$ are each, independently, H, halo, $C_1$-$C_4$ alkyl, $C_1$-$C_4$ haloalkyl, hydroxy, CN, or NO$_2$; and $R^{7a}$, $R^{7b}$, $R^{8a}$, and $R^{8b}$ are each H.

In some embodiments, (H) when $R^2$ is $C_1$-$C_4$ alkyl, —CH$_2$—O—($C_1$-$C_4$ alkyl), or CH$_2$OH, then $R^3$ and $R^6$ are not both H; and In some embodiments, (I) when $R^2$ is CH$_3$, then $R^3$, $R^4$, and $R^6$ are each H and $R^5$ is not H or isopropyl.

In further embodiments, $R^1$ is H.

In further embodiments, $R^1$ is $C_1$-$C_8$ alkyl.

In further embodiments, $R^2$ is $C_1$-$C_4$ alkyl or $C_1$-$C_4$ haloalkyl.

In further embodiments, $R^2$ is methyl, ethyl, isopropyl, n-butyl, or CF$_3$.

In further embodiments, $R^3$, $R^4$, $R^5$, and $R^6$ are each, independently, H, methyl, NH$_2$, CN, halo, CF$_3$, NO$_2$, or OH.

In further embodiments of the invention, $R^{7a}$, $R^{7b}$, $R^{8a}$, and $R^{8b}$ are each H.

In further embodiments of the invention, $R^3$ and $R^6$ are each H.

In further embodiments of the invention, $R^3$, $R^5$, and $R^6$ are each H.

In further embodiments of the invention, $R^4$ is halo.

In further embodiments of the invention, $R^4$ is Cl.

In further embodiments of the invention, $R^2$ is $C_1$-$C_4$ alkyl.

In further embodiments of the invention, $R^2$ is methyl.

In further embodiments of the invention, $R^1$ is H.

In further embodiments of the invention, $R^1$ is H or $C_1$-$C_4$ alkyl, $R^2$ is $C_1$-$C_4$ alkyl, $R^3$ is H, $R^4$ is halo, $R^5$ is H, $R^6$ is H, $R^{7a}$ is H, $R^{7b}$ is H, $R^{8a}$ is H, and $R^{8b}$ is H.

In further embodiments of the invention, $R^1$ is H, $R^2$ is Me, $R^3$ is H, $R^4$ is Cl, $R^5$ is H, $R^6$ is H, $R^{7a}$ is H, $R^{7b}$ is H, $R^{8a}$ is H, and $R^{8b}$ is H.

In further embodiments of the invention, L is halo.

In further embodiments of the invention, L is hydroxy.

In further embodiments of the invention, L is Cl.

In further embodiments of the invention, L is Br.

In further embodiments of the invention, L is —OSO$_2$R such as sulfonates (e.g., mesylate, triflate, methyl sulfonate).

In further embodiments of the invention, L is —OSi(R')$_3$ such as trimethylsilyloxy.

In further embodiments of the invention, the compound of Formula I has an S configuration at the carbon bearing $R^2$.

In further embodiments of the invention, the compound of Formula I has an R configuration at the carbon bearing $R^2$.

The present invention provides a process for preparing a compound of Formula I:

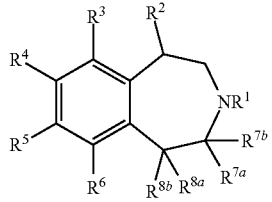

I or salt form thereof,
comprising reacting a compound of Formula II:

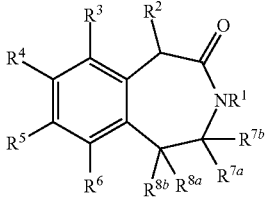

II with a reducing agent optionally in the presence of a Lewis acid for a time and under conditions suitable for forming the compound of Formula I or salt form thereof.

In some embodiments, the reducing agent comprises a borane such as $BH_3$. In further embodiments, the reducing agent comprises a metal hydride such as a borohydride or aluminum hydride. In some embodiments, the reducing agent is $BH_3$:THF. Other reducing agents are suitable and can be selected by one skilled in the art. Example suitable reducing agents are compounds that selectively reduce the amide moiety of the compound of Formula II.

In further embodiments, a Lewis acid can be present in the reaction in an amount sufficient to increase reaction rate. Suitable Lewis acids include boron-containing Lewis acids such as $BF_3$ and adducts thereof including $BF_3$:TBME (t-butyl methyl ether); $BF_3$:$OEt_2$; $BF_3$:$O(CH_2CH_2CH_2CH_3)_2$; $BF_3$:THF; and the like. Suitable amounts include from about 0.01 eq to about 1 eq relative to amount of compound of Formula II.

Due to potential sensitivity of the reducing agent to air, the reaction can be conducted under an inert atmosphere.

Reacting can be carried out in any inert solvent such as a dialkylether or cyclic ether (e.g., THF) at any suitable temperature, such as room temperature. The duration of the reduction can be carried out for any amount of time determined by one skilled in the art. In some embodiments, the reaction duration is sufficient to allow the reaction to go substantially to completion. For example, reaction durations can range from about 10 minutes to about 48 hours. In some embodiments, the reaction duration is about 8-12 hours. Reaction completion can be monitored, for example, by LC/MS.

The amount of reducing agent provided is typically sufficient to provide at least enough reducing equivalents to reduce the compound of Formula II to the desired product. For example, an excess of reducing agent can be provided such as about 10×, about 5×, about 3×, or about 2× reducing equivalent excess. For boranes and related reducing agents, the molar ratio of reducing agent to the compound of Formula II can be, for example, about 2:1, about 3:1, about 5:1, or about 10:1. In some embodiments, the molar ratio is about 3:1.

In some embodiments, the yield for the reduction reaction (based on amount of compound of Formula II), is greater than about 50%, about 60%, about 70%, about 80%, or about 90%.

The present invention further provides a process for preparing a compound of Formula II, or salt form thereof, comprising reacting a compound of Formula III:

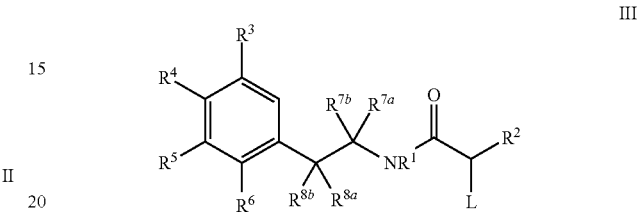

III or salt form thereof, with a cyclizing reagent for a time and under conditions suitable for forming the compound of Formula II or salt form thereof.

In some embodiments, L of the compound of Formula III is halo. In further embodiments, L of the compound of Formula III is Cl.

In some embodiments, the cyclizing reagent includes a Lewis acid, such as, for example, a $C_1$-$C_8$ alkyl aluminum halide (e.g., methyl aluminum chloride, ethyl aluminum chloride, etc.), a $C_2$-$C_{16}$ dialkyl aluminum halide (e.g., dimethyl aluminum chloride, diethyl aluminum chloride, etc.), trialkylaluminum, $AlCl_3$, or $AlBr_3$. In some embodiments, the cyclizing reagent is $AlCl_3$. Other suitable cyclizing reagents include acids such as sulfuric acid.

Cyclization can be carried out in the absence of solvent or in the presence of solvent. Suitable solvents include nonpolar or weakly polar solvents such as decahydronaphthalene or 1,2-dichlorobenzene. Other suitable solvents include haloalkanes and other halogenated aromatics such as 1,3-dichlorobenzene and 1,4-dichlorobenzene.

The cyclizing reagent can be provided in an amount suitable for maximizing the yield of the cyclized product. In some embodiments, the cyclizing reagent can be provided in molar excess relative to the amount of compound of Formula III. Example molar ratios of cyclizing reagent to compound of Formula III include about 2:1, about 3:1, about 5:1, or about 10:1. In some embodiments, the molar ratio is about 3:1.

In further embodiments, cyclization is carried out at elevated temperature such as at about 80 to about 160° C. In some embodiments, cyclization is carried out at about 150° C. The cyclization reaction can be monitored by LC/MS. Duration to substantial completion can be about 10 minutes to about 24 hours. In some embodiments, reaction duration is from about 3 hours to about 15 hours.

In some embodiments, the yield for the cyclization reaction (based on amount of compound of Formula III), is greater than about 40%, about 50%, about 60%, about 70%, about 80%, or about 90%.

The present invention further provides preparing a compound of Formula III comprising reacting a compound of Formula IV:

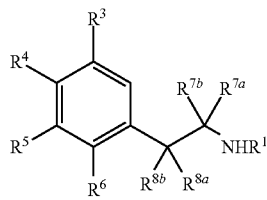

or salt form thereof, with a compound of Formula:

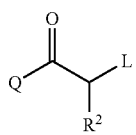

wherein Q is a leaving group, for a time and under conditions suitable for forming the compound of Formula III or salt form thereof.

According to some embodiments, Q is hydroxy, alkoxy, halo, or $O(CO)R^Q$, wherein $R^Q$ is $C_1$-$C_8$ alkyl, $C_3$-$C_7$ cycloalkyl, aryl, heteroaryl, or heterocycloalkyl. In some embodiments, Q is halo such as Cl. In other embodiments, Q is hydroxy. In yet other embodiments, Q is alkoxy, such as methoxy, ethoxy, or t-butoxy.

Amide formation can be optionally carried out in the presence of base such as an amine (e.g., $NMe_3$, $NEt_3$, morpholine, pyridine, diisopropylethylamine, piperidine, N,N-dimethylaminopiperidine, and the like). Other suitable bases include inorganic bases such as NaOH, KOH, CsOH, and the like.

Relative amounts of reagents suitable for carrying out the reaction include about molar equivalents of each. For example, the amide formation reaction can be carried out with a molar ratio of compound of Formula IV to compound of Formula:

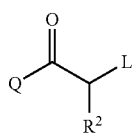

of about 1:1. In further embodiments, an equivalent amount of base can also be included (e.g., molar ratio of about 1:1:1). In yet further embodiments, base can be added in excess relative to the amount of compound of Formula IV.

In further embodiments, the amide formation reaction can be carried out in solvent, such a polar solvent. An example of a polar solvent is acetonitrile. Reaction temperature can vary from about 10 to about 30° C. In some embodiments, the reaction can start at a temperature below room temperature such as about 0° C., and for the reaction duration, rise to about room temperature. Reaction progress can be monitored, for example, by TLC, and time to completion can be from about 10 minutes to about 5 hours, depending on, for example, scale of the reaction.

In some embodiments, the yield for the amide formation reaction (based on amount of compound of Formula IV), is greater than about 40%, about 50%, about 60%, about 70%, about 80%, or about 90%.

In an alternate route to compounds of Formula I, the present invention provides a process for preparing a compound of Formula I:

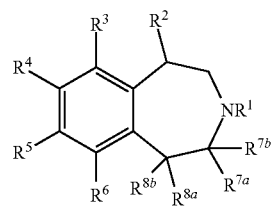

or salt form thereof, comprising reacting a compound of Formula IIIa:

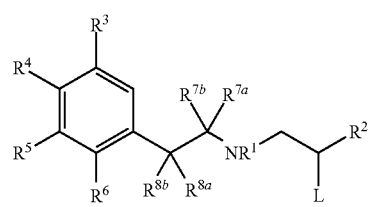

with a cyclizing reagent for a time and under conditions suitable for forming the compound of Formula I.

In some embodiments, L of the compound of Formula IIIa is halo. In further embodiments, L of the compound of Formula IIIa is Br or Cl.

In some embodiments, the cyclizing reagent includes a Lewis acid, such as, for example, a $C_1$-$C_8$ alkyl aluminum halide (e.g., methyl aluminum chloride, ethyl aluminum chloride, etc.), a $C_2$-$C_{16}$ dialkyl aluminum halide (e.g., dimethyl aluminum chloride, diethyl aluminum chloride, etc.), trialkylaluminum. $AlCl_3$, or $AlBr_3$. Other suitable cyclizing reagents include acids such as sulfuric acid.

Cyclization can be carried out in the absence of solvent or in the presence of solvent. Suitable solvents include nonpolar or weakly polar solvents such as decahydronaphthalene or 1,2-dichlorobenzene. Other suitable solvents include haloalkanes and other halogenated aromatics such as 1,3-dichlorobenzene and 1,4-dichlorobenzene.

The cyclizing reagent can be provided in an amount suitable for maximizing the yield of the cyclized product. In some embodiments, the cyclizing reagent can be provided in molar excess relative to the amount of compound of Formula IIIa. Example molar ratios of cyclizing reagent to compound of Formula IIIa include about 2:1, about 3:1, about 5:1, or about 10:1. In some embodiments, the molar ratio is about 3:1.

In further embodiments, cyclization is carried out at elevated temperature such as at about 80 to about 160° C. In some embodiments, cyclization is carried out at about 140° C. The cyclization reaction can be monitored by LC/MS. Duration to completion can be about 10 minutes to about 24 hours. In some embodiments, reaction duration is from about 3 hours to about 15 hours.

In some embodiments, the yield for the cyclization reaction (based on amount of compound of Formula IIIa), is greater than about 40%, about 50%, about 60%, about 70%, about 80%, or about 90%.

The present invention further provides a process for preparing a compound of Formula IIIa, or salt form thereof, comprising reacting a compound of Formula III:

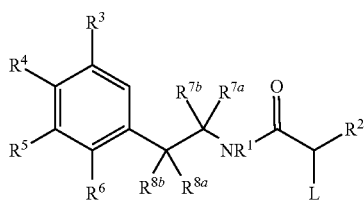

III with a reducing agent optionally in the presence of a Lewis acid for a time and under conditions suitable for forming said compound of Formula IIIa.

In some embodiments, the reduction of III can be carried out so that the stereochemistry of one or more chiral centers present in the compound of Formula III is substantially retained in the reduced product (Formula IIIa). In further embodiments, the reduction of IIIa can be carried out using a substantially pure stereoisomer of IIIa. In yet further embodiments, the reduction of IIIa can be carried out using a substantially pure stereoisomer of IIIa and result in a substantially pure stereoisomer of III. For example, a compound of Formula III having ee of greater than about 80, about 90, or about 95% can reduced to form a compound of Formula IIIa having a similar ee.

In some embodiments, the reducing agent comprises a borane such as $BH_3$. In further embodiments, the reducing agent comprises a metal hydride such as a borohydride or aluminum hydride. In some embodiments, the reducing agent is $BH_3$:THF. Other reducing agents are suitable and can be selected by one skilled in the art. Example suitable reducing agents are compounds that selectively reduce the amide moiety of the compound of Formula II.

In further embodiments, a Lewis acid can be present in the reaction in an amount sufficient to increase reaction rate. Suitable Lewis acids include boron-containing Lewis acids such as $BF_3$ and adducts thereof including $BF_3$:TBME (t-butyl methyl ether); $BF_3$:$OEt_2$; $BF_3$:$O(CH_2CH_2CH_2CH_3)_2$; $BF_3$:THF; and the like. Suitable amounts include from about 0.01 eq to about 1 eq relative to amount of compound of Formula III.

Due to potential sensitivity of the reducing agent to air, the reaction can be conducted under an inert atmosphere.

The reduction reaction can be carried out in inert solvent such as a dialkylether or cyclic ether (e.g., THF) at any suitable temperature, such as room temperature. The duration of the reduction can be carried out for any amount of time. In some embodiments, the reaction duration is sufficient to allow the reaction to go substantially to completion. For example, reaction durations can range from about 10 minutes to about 72 hours. In some embodiments, the reaction duration is about 8-12 hours. Reaction completion can be monitored, for example, by LC/MS.

The amount of reducing agent provided is typically sufficient to provide at least enough reducing equivalents to reduce the compound of Formula II to the desired product. For example, an excess of reducing agent can be provided such as about 10×, 5×, 3×, or 2× reducing equivalent excess. For boranes and related reducing agents, the molar ratio of reducing agent to the compound of Formula II can be, for example, 2:1, 3:1, 5:1, or 10:1. In some embodiments, the molar ratio is 3:1.

In some embodiments, the yield for the reduction reaction (based on amount of compound of Formula III), is greater than about 50%, about 60%, about 70%, about 80%, or about 90%.

The present invention further provides processes provided below in Schemes Ia, Ib and Ic, wherein constituent members of the structures depicted therein are defined above.

Scheme Ia

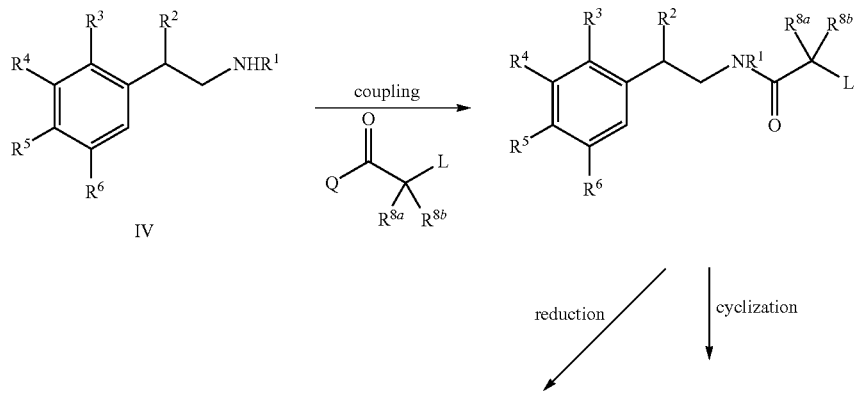

-continued
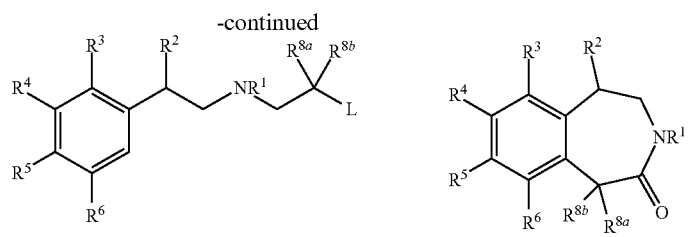
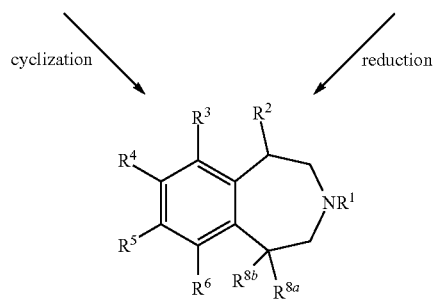
Scheme Ib
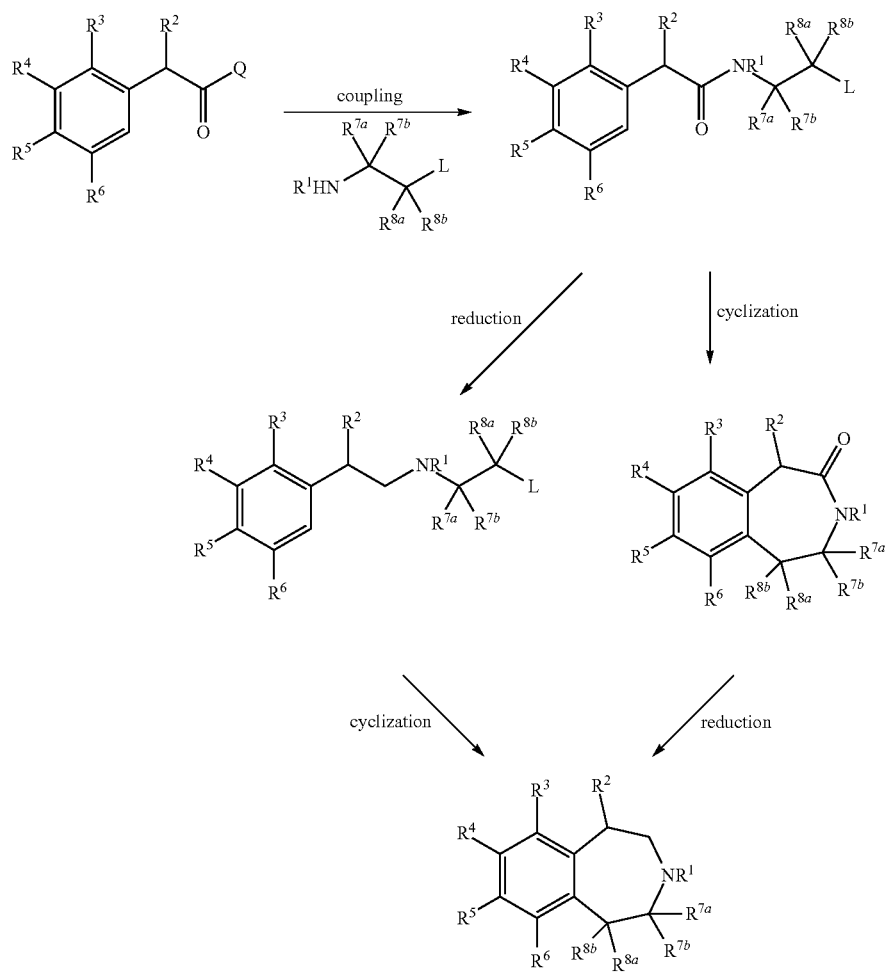

Scheme Ic

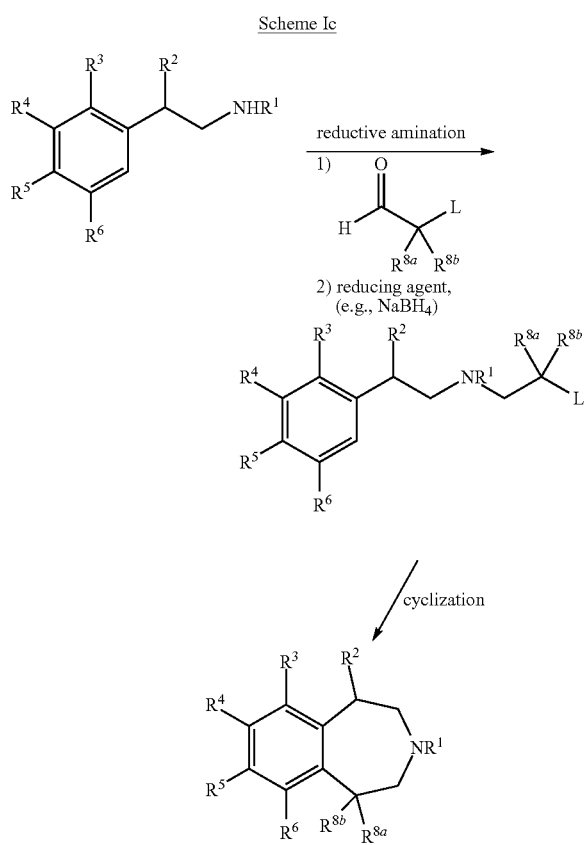

In further embodiments, the present invention provides a method of resolving a mixture of compounds of Formulas Ia and Ib:

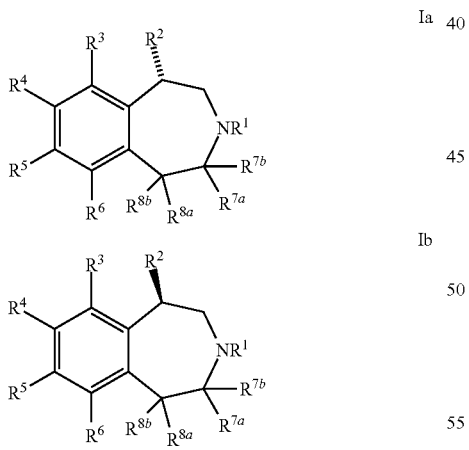

Ia

Ib by contacting the mixture of compounds with a chiral resolving acid enriched in one stereoisomer (e.g., ee greater than about 50%, about 75%, about 90% or about 95%) to form chiral resolving acid salts of the compounds of the mixture, and then precipitating the chiral resolving acid salts. The resulting precipitate is typically enriched in the chiral resolving acid salt of one of the compounds of Formulas Ia or Ib (e.g., ee>50%). In some embodiments, the precipitate is enriched in the chiral resolving acid salt form of the compound of Formula Ia. In some embodiments, the precipitate is enriched in the chiral resolving acid salt form of the compound of Formula Ib. In further embodiments, the chiral resolving acid is a stereoisomer of toluoyl tartaric acid, camphoric acid, ketogulonic acid, or tartaric acid. In further embodiments, the chiral resolving acid is a stereoisomer of tartaric acid such as L-(+)-tartaric acid.

Contacting of compounds with a chiral resolving acid can be carried out in solution. Suitable solvents support dissolution of both the chiral resolving acid and the compounds of Formulas Ia and Ib. Some example solvents include polar solvents or water-miscible solvents such as alcohols (e.g., methanol, ethanol, isopropanol, t-butanol, and the like), isopropylacetate, water, and mixtures thereof. In further embodiments, the solvent contains a mixture of t-butanol and water. Some example mixtures include about 5-25% water and about 75-95% t-butanol. In some embodiments, the solvent contains about 8-12% water and about 88-92% of t-butanol.

Precipitate containing the chiral resolving acid salt forms can be formed by precipitation from any suitable solvent which dissolves the salts such as the solvent in which contacting was carried out. Precipitation can be induced by any method known in the art such as by heating a solution containing the mixture of salts followed by cooling. Precipitate can be separated from the solvent by, for example, filtration. Enrichment of the precipitate in one chiral salt over the other can be characterized by an enantiomeric excess (ee) of greater than about 50%, about 60%, about 70%, about 80%, about 90%, about 95%, about 98%, or about 99%. In some embodiments, ee is greater than about 80%. Precipitation can be repeated one or more times to increase the proportion of a chiral salt in the precipitate by re-dissolving and re-precipitating previously obtained precipitate.

The present invention further provides a chiral resolving acid salt of a compound of Formula Ia or Ib:

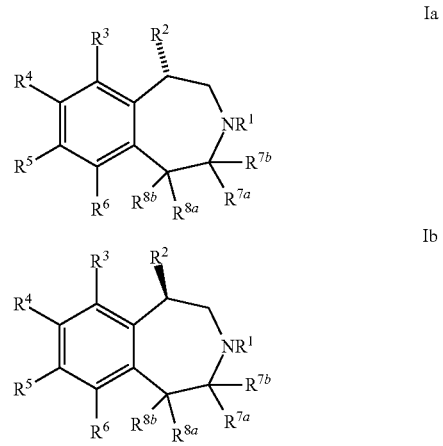

Ia

Ib wherein constituent members are defined hereinabove. Compositions of the present invention can contain one or both the salt form of a compound of Formula Ia and the salt form of a compound of Formula Ib. In some embodiments, the salt form of the compound of Formula Ia is present in the composition in an amount greater than the salt form of a compound of Formula Ib. In other embodiments, the salt form of the compound of Formula Ib is present in the composition in an amount greater than the salt form of a compound of Formula Ia.

Further example processes and intermediates of the present invention are provided below in Scheme II, where constituent members of compounds depicted therein are defined hereinbelow. The symbol "*" designates optionally chiral centers that can be substantially retained or inverted over the course of the depicted reactions.

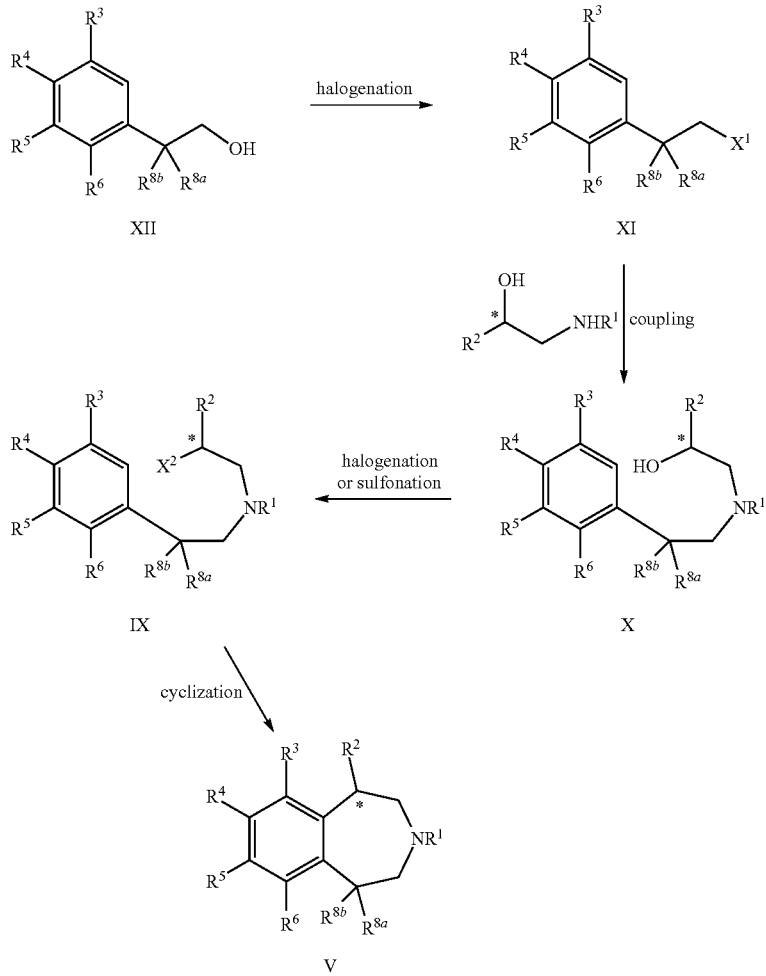

Scheme II

In a second aspect of the present invention are provided processes, such as are exemplified by Scheme II, that involve compounds of Formulas V, Va, Vb, IX, X, XI, and XII, or salt forms thereof, wherein:

$R^1$ is H or $C_1$-$C_8$ alkyl;

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;

$R^3$, $R^4$, $R^5$, and $R^6$ are each, independently, H, halo; $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, $OR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;

$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;

$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and $R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;

$X^1$ is a leaving group;

$X^2$ is halo or $SO_2R''$; and $R''$ is $C_1$-$C_8$ alkyl, aryl, or heteroaryl each optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy.

In some embodiments of the invention:

$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, or $CH_2OH$;

$R^3$ and $R^6$ are each H;

$R^4$ and $R^5$ are each, independently, H, halo, $C_1$-$C_8$ haloalkyl, hydroxy, $OR^9$, $SR^9$, alkoxyalkyl, $NHR^{10}$, $NR^{10}R^{11}$, aryl, or heteroaryl, wherein said aryl can be substituted with up to two substituents selected from $C_1$-$C_8$ alkyl, halo, $C_1$-$C_8$ haloalkyl, and alkoxy, and said heteroaryl can be optionally substituted with up to two substituents selected from halogen and $C_1$-$C_8$ alkyl; or $R^4$ and $R^5$ together with the atoms to which they are attached form a 5- or 6-member heterocyclic ring having one O atom;

$R^{7a}$ is H;
$R^{7b}$ is H or $C_1$-$C_8$ alkyl;
$R^{8a}$ and $R^{8b}$ are each H; and
$R^{10}$ and $R^{11}$ are each, independently, $C_1$-$C_8$ alkyl, $C_1$-$C_8$ alkenyl, $C_1$-$C_8$ haloalkyl, aryl, heteroaryl, aralkyl, heteroarylalkyl, or allyl.

In some embodiments, (A) if $R^2$ is methyl and $R^4$ is H, then $R^5$ is not thiazole, substituted thiazole or a thiazole derivative.

In some embodiments, (B) if $R^{7a}$ is H and $R^{7b}$ is other than H, then neither $R^4$ nor $R^5$ can be H.

In some embodiments, (C) if $R^1$ and $R^2$ are methyl, and $R^5$ is H then $R^4$ is not $NHR^{10}$ or $NR^{10}R^{11}$.

In some embodiments, (D) if $R^1$ and $R^2$ are methyl and $R^5$ is H, then $R^4$ is not imidazolyl, substituted imidazolyl, or an imidazole derivative.

In some embodiments, (E) if $R^1$ is H or $CH_3$, and $R^2$ is $CH_3$ or OH, then $R^3$, $R^4$, $R^5$, and $R^6$ cannot all be H.

In some embodiments, (F) if $R^1$ is H and $R^2$ is isopropyl or OH, then $R^4$ and $R^5$ cannot both be $OCH_3$ or OH.

In some embodiments, (G) if $R^1$ is $CH_3$ and $R^2$ is n-propyl, then $R^4$ cannot be OH, $R^5$ cannot Cl, and $R^3$ and $R^6$ cannot both be H.

In further embodiments, $R^1$ is H.
In further embodiments, $R^1$ is $C_1$-$C_8$ alkyl.
In further embodiments, $R^2$ is methyl, ethyl, n-propyl, or isopropyl.
In further embodiments, $R^2$ is methyl.
In further embodiments, $R^4$ is Cl, Br, haloalkyl, $CF_3$, thiophenyl, furanyl, pyrrolyl, pyrazolyl, or imidazolyl.
In further embodiments, $R^4$ is Cl.
In further embodiments, $R^5$ is methoxy, ethoxy, n-propoxy, isopropoxy, allyloxy, thiophenyl, furanyl, pyrrolyl, pyrazolyl, imidazolyl, or phenyl, wherein said imidazolyl is optionally substituted by one or more halo or methyl and said phenyl is optionally substituted with up to two substituents selected from $C_1$-$C_8$ alkyl, $C_1$-$C_8$ haloalkyl, halo, and alkoxy.
In further embodiments, $R^5$ is H.

In some embodiments:
$R^2$ is $C_1$-$C_4$ alkyl, —$CH_2$—O—($C_1$-$C_4$ alkyl), $C_1$-$C_4$ haloalkyl, or $CH_2OH$;
$R^3$, $R^4$, $R^5$, and $R^6$ are each, independently, H, halo, $C_1$-$C_4$ alkyl, $C_1$-$C_4$ haloalkyl, hydroxy, $NH_2$, CN, or $NO_2$; and
$R^{7a}$, $R^{7b}$, $R^{8a}$, and $R^{8b}$ are each H.

In some embodiments, (H) when $R^2$ is $C_1$-$C_4$ alkyl, —$CH_2$—O—($C_1$-$C_4$ alkyl), or $CH_2OH$, then $R^3$ and $R^6$ are not both H.

In some embodiments, (I) when $R^2$ is $CH_3$, then $R^3$, $R^4$, and $R^6$ are each H and $R^5$ is not H or isopropyl.

In further embodiments, $R^1$ is H.
In further embodiments, $R^1$ is $C_1$-$C_8$ alkyl.
In further embodiments, $R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), or $C_1$-$C_4$ haloalkyl;
In further embodiments, $R^2$ is $C_1$-$C_4$ alkyl or $C_1$-$C_4$ haloalkyl.
In further embodiments, $R^2$ is methyl, ethyl, isopropyl, n-butyl, or $CF_3$.
In further embodiments, $R^3$, $R^4$, $R^5$, and $R^6$ are each, independently, H, methyl, $NH_2$, CN, halo, $CF_3$, $NO_2$, or OH.

In further embodiments of the invention, $R^{7a}$, $R^{7b}$, $R^{8a}$, and $R^{8b}$ are each H.
In further embodiments of the invention, $R^3$ and $R^6$ are each H.
In further embodiments of the invention, $R^3$, $R^5$, and $R^6$ are each H.
In further embodiments of the invention, $R^4$ is halo.
In further embodiments of the invention, $R^4$ is Cl.
In further embodiments of the invention, $R^2$ is $C_1$-$C_4$ alkyl.
In further embodiments of the invention, $R^2$ is methyl.
In further embodiments of the invention, $R^1$ is H.
In further embodiments, $X^1$ is halo.
In further embodiments, $X^1$ is Br.
In further embodiments, $X^1$ is Cl.
In further embodiments, $X^2$ is halo.
In further embodiments, $X^2$ is Br.
In further embodiments, $X^2$ is Cl.
In further embodiments of the invention, $R^1$ is H or $C_1$-$C_4$ alkyl, $R^2$ is $C_1$-$C_4$ alkyl, $R^3$ is H, $R^4$ is halo, $R^5$ is H, $R^6$ is H, $R^{7a}$ is H, $R^{7b}$ is H, $R^{8a}$ is H, and $R^{8b}$ is H.

In further embodiments of the invention, $R^1$ is H, $R^2$ is Me, $R^3$ is H, $R^4$ is Cl, $R^5$ is H, $R^6$ is H, $R^{7a}$ is H, $R^{7b}$ is H, $R^{8a}$ is H, and $R^{8b}$ is H.

In further embodiments of the invention, the compound of Formula V has an S configuration at the carbon bearing $R^2$.

In further embodiments of the invention, the compound of Formula V has an R configuration at the carbon bearing $R^2$.

The present invention provides a process for preparing a compound of Formula V:

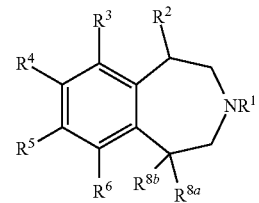

V or salt thereof, by reacting a compound of Formula IX:

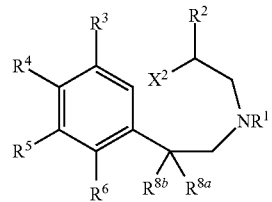

IX or salt thereof, with a cyclizing reagent for a time and under conditions suitable for forming the compound of Formula V.

In some embodiments, the cyclizing reagent includes a Lewis acid, such as, for example, a $C_1$-$C_8$ alkyl aluminum halide (e.g., methyl aluminum chloride, ethyl aluminum chloride, etc.), a $C_2$-$C_{16}$ dialkyl aluminum halide (e.g., dimethyl aluminum chloride, diethyl aluminum chloride, etc.), trialkylaluminum, $AlCl_3$, or $AlBr_3$. Other suitable cyclizing reagents include acids such as sulfuric acid.

The cyclizing reagent can be provided in an amount suitable for maximizing the yield of the cyclized product. In some embodiments, the cyclizing reagent can be provided in molar excess relative to the amount of compound of Formula IX.

Example molar ratios of cyclizing reagent to compound of Formula IX include about 1.5:1, about 2:1, about 3:1, about 5:1, or about 10:1. In some embodiments, the molar ratio is about 1.5:1.

Reacting can be carried out in the presence of any suitable solvent (or in the absence of solvent) such as a non-polar or weakly-polar solvent or a high boiling solvent (boiling point greater than for water). In some embodiments, reacting can be carried out in the presence of 1,2-dichlorobenzene. In further embodiments, reacting can be carried out in the presence of decalin.

Reaction temperature can be any suitable temperature such as temperatures that do not readily degrade the reactants yet maximize reaction efficiency and/or minimize reaction time. In some embodiments, reacting is carried out at an elevated temperature such as, for example, between about 80 and about 170° C. In some embodiments, elevated temperature is from about 100 to about 150, about 120 to about 150, or about 140° C.

The cyclization reaction can be monitored by LC/MS. Duration to completion can be about 10 minutes to about 24 hours. In some embodiments, reaction duration is from about 3 hours to about 15 hours. In further embodiments, reaction duration is about 2 to 5 hours.

In some embodiments, the yield for the cyclization reaction (based on amount of compound of Formula IX), is greater than about 40%, about 50%, about 60%, about 70%, about 80%, or about 90%.

The present invention further provides a process for preparing a compound of Formula IX:

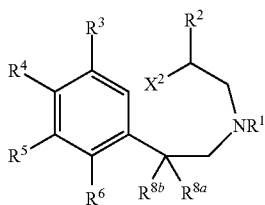

IX or salt thereof, by reacting a compound of Formula X:

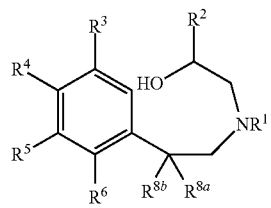

X or salt thereof, with a halogenating/sulfonating reagent for a time and under conditions suitable for forming the compound of Formula XI.

Suitable halogenating/sulfonating reagents are capable of replacing the OH moiety in the compound of Formula X with a halogen atom or sulfonate moiety. In some embodiments, the halogenating/sulfonating reagent is $SOBr_2$ or $SOCl_2$.

The halogenating/sulfonating reagent can be provided in an amount sufficient to theoretically produce maximum yield. Suitable molar ratios of halogenating/sulfonating reagent to compound of Formula X include the ratios of about 10:1, about 5:1, about 3:1, about 2:1, or about 1.5:1. In some embodiments, the molar ratio is about 1.06:1 to about 1.4:1.

Reacting can be carried out in any suitable solvent or in the absence of solvent, such as solvents capable of dissolving at least one of the compound of Formula X or the halogenating/sulfonating reactant. In some embodiments, the solvent contains DMF (dimethylformamide). In further embodiments, the solvent contains toluene. In yet further embodiments, the solvent contains dichloromethane. In some embodiments, the solvent contains dimethylformamide and toluene, and in further embodiments, the solvent contains dimethylformamide and dichloromethane.

Any reaction temperature that does not substantially decompose the starting materials, solvent, or products is suitable. In some embodiments, reacting is carried out at temperatures such as from about −40 to about 80° C., about −10 to about 30° C. or about 0° C. to about room temperature.

In some embodiments, the compound of Formula XI is isolated, such as by recrystallization from a suitable solvent. Yield can be greater than about 20%, greater than about 30%, greater than about 40%, or greater than about 50%. In some embodiments, yield is greater than about 50%.

The present invention also provides a process for preparing a compound of Formula X:

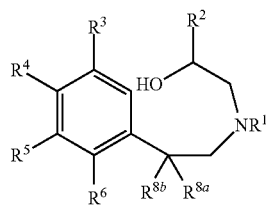

X or salt thereof,
comprising reacting a compound of Formula XI:

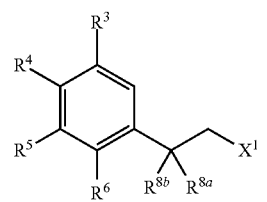

XI with a compound of Formula:

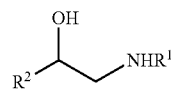

for a time and under conditions suitable for forming the compound of Formula X.

The reacting can be carried out, for example, at elevated temperature such as from about 80 to about 110° C. or 90 to about 10° C. In some embodiments, reacting is carried out at about 95° C.

Any suitable inert solvent can be used, and in some embodiments, reacting is carried out in the absence of solvent.

A sufficient amount of compound of Formula:

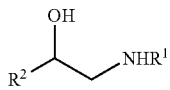

can be provided in the reaction to obtain a theoretical or empirical maximum yield. Example amounts can range from at least about 1 molar equivalent to any amount that would be in molar excess (e.g., about 10× or 15×) relative to the amount of compound of Formula XI.

An example reaction duration can be from about 3 to about 5 hours.

The present invention further provides a process of preparing a compound of Formula XI by reacting a compound of Formula XII:

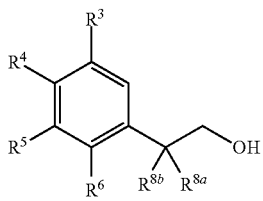

with a halogenating/sulfonating reagent for a time and under conditions suitable for forming the compound of Formula XI.

The halogenating/sulfonating reagent can be any suitable reagent capable of replacing the hydroxy moiety of the compound of Formula XII with a suitable leaving group such as a halogen atom or sulfonate moiety. In some embodiments, the halogenating/sulfonating reagent is, for example, $PBr_3$ or $PCl_3$.

Any suitable solvent can be used or the reacting can be carried out in the absence of solvent.

Reaction temperature can be readily selected by the art skilled. In some embodiments, reacting is carried out at lowered temperatures such as from about −20 to about 15° C., about −10 to about 10° C., or about 0° C. In some embodiments, the reaction temperature is below about 10° C.

Halogenating/sulfonating reagent can be provided in an amount sufficient to produce maximum theoretical yield. For example, the molar ratio of halogenating/sulfonating reagent to compound of Formula XII can range from about 20:1 to about 0.2:1. In some embodiments, halogenating/sulfonating reagent is provided in slight excess, such as in a ratio of about 1:1 or about 0.5:1.

Reaction yield can be greater than about 75%, greater than about 85%, greater than about 90%, greater than about 95, or greater than about 98%. In some embodiments, yield is from about 95% to about 100%.

In further embodiments, the present invention provides a method of resolving a mixture of compounds of Formulas Va and Vb:

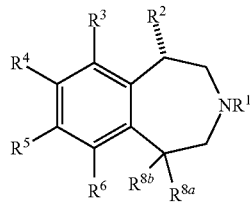

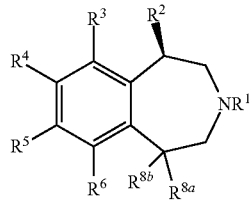

by contacting the mixture of compounds with a chiral resolving acid enriched in one stereoisomer (e.g., ee greater than about 50%, about 75%, about 90% or about 95%) to form chiral resolving acid salts of the compounds of the mixture, and then precipitating the chiral resolving acid salts. The resulting precipitate is typically enriched in the chiral resolving acid salt of one of the compounds of Formulas Va or Vb (e.g., ee>50%). In some embodiments, the precipitate is enriched in the chiral resolving acid salt form of the compound of Formula Va. In some embodiments, the precipitate is enriched in the chiral resolving acid salt form of the compound of Formula Vb. In further embodiments, the chiral resolving acid is a stereoisomer of toluoyl tartaric acid, camphoric acid, ketogulonic acid, or tartaric acid. In further embodiments, the chiral resolving acid is tartaric acid such as L-(+)-tartaric acid.

Contacting of compounds of Formulas Va and Vb with a chiral resolving acid can be carried out in solution. Suitable solvents support dissolution of both the chiral resolving acid and the compounds of Formulas Va and Vb. Some example solvents include polar solvents or water-miscible solvents such as alcohols (e.g., methanol, ethanol, isopropanol, t-butanol, 1-butanol and the like), isopropylacetate, tetrahydrofuran, acetone, methyl isobutyl ketone, water, and mixtures thereof. In some embodiments, the solvent contains a mixture of alcohol and water. In further embodiments, the solvent contains a mixture of t-butanol and water. Some example mixtures include about 5-25% water and about 75-95% t-butanol. In some embodiments, the solvent contains about 8-12% water and about 88-92% of t-butanol. In some embodiments, the solvent contains a mixture of acetone and water.

Precipitate containing the chiral resolving acid salt forms can be formed by precipitation from any suitable solvent which dissolves the salts such as the solvent in which contacting was carried out. Precipitation can be induced by any method known in the art such as by heating a solution containing the mixture of salts followed by cooling. Precipitate can be separated from the solvent by, for example, filtration. Enrichment of the precipitate in one chiral salt over the other can be characterized by an enantiomeric excess (ee) of greater than about 50%, about 60%, about 70%, about 80%, about 90%, about 95%, about 98%, or about 99%. In some embodiments, ee is greater than about 80%. Precipitation can be repeated one or more times to increase the proportion of a chiral salt in the precipitate by re-dissolving and re-precipitating previously obtained precipitate.

The present invention further provides a chiral resolving acid salt of a compound of Formula Va or Vb:

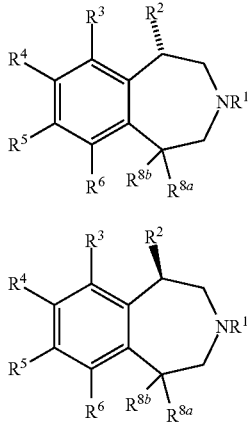

wherein constituent members are defined hereinabove. Compositions of the present invention can contain one or both the salt form of a compound of Formula Va and the salt form of a compound of Formula Vb. In some embodiments, the salt form of the compound of Formula Va is present in the composition in an amount greater than the salt form of a compound of Formula Vb. In other embodiments, the salt form of the compound of Formula Vb is present in the composition in an amount greater than the salt form of a compound of Formula Va.

The present invention further provides a hydrochloric acid salt of a compound of Formula Va or Vb and compositions thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl."

As used herein, "aryl" refers to monocyclic or polycyclic aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic hydrocarbons including cyclized alkenyl, and alkynyl groups. Cycloalkyl groups can include mono-, bi- or poly-cyclic ring systems as well as double and triple bonds. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, hexane, and the like.

As used herein, "heteroaryl" groups are monocyclic and polycyclic aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms.

As used herein, "heterocycloalkyl" refers to a cycloalkyl group wherein one or more of the ring-forming carbon atoms is replaced by a heteroatom such as an O, S, N, or P atom. Also included in the definition of heterocycloalkyl are moieties that have one or more aromatic rings fused having a bond in common with) to the nonaromatic heterocyclic ring, for example phthalimidyl, naphthalimidyl pyromellitic diimidyl, phthalanyl, and benzo derivatives of saturated heterocycles such as indolene and isoindolene groups.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "thioalkoxy" refers to an alkoxy group in which the O atom is replaced by an S atom.

As used herein, "aryloxy" refers to an —O-aryl group. An example aryloxy group is phenoxy.

As used herein, "thioaryloxy" refers to an aryloxy group in which the O atom is replaced by an S atom.

As used herein, "aralkyl" refers to an alkyl moiety substituted by an aryl group. Example aralkyl groups include benzyl, phenethyl, and naphthylmethyl groups. In some embodiments, arylalkyl groups have from 7 to 20 or 7 to 11 carbon atoms.

As used herein, "hydroxyalkyl" refers to an alkyl group substituted by hydroxy.

As used herein, "alkoxyalkyl" refers to an alkyl group substituted by an alkoxy group.

As used herein, the term "reacting" is used as known in the art and generally refers to the bringing together of chemical reagents in such a manner so as to allow their interaction at the molecular level to achieve a chemical or physical transformation.

As used herein, the term "substituted" refers to the replacement of a hydrogen moiety with a non-hydrogen moiety in a molecule or group.

As used herein, the term "thiazole derivative" refers to a moiety containing a thiazolyl group.

As used herein, the term "imidazole derivative" refers to a moiety containing a imidazolyl group.

As used herein, the term "contacting" refers to the bringing together of substances so that they can interact at the molecular level.

As used herein, the term "reducing agent" is used as known in the art and refers to any chemical reagent that carries out the reduction of another chemical reagent. In some embodiments, a reduction carried out by a reducing agent involves lowering the number of bonds of an atom (e.g., a C atom) to oxygen or sulfur. For example, a reducing agent can convert (or reduce) a ketone to an alcohol. In some embodiments, the reducing agent converts an amide to an amine. Numerous reducing agents are known in the art and can be identified by comparing redox potentials of the reducing agent and the substance to be reduced. Typically, a reducing agent has a lower reducing potential than the substance to be reduced. Methods for measuring redox potentials are well known in the art. In other embodiments, the reducing agent can be an oxo acceptor. Example reducing agents include metal hydrides such as borohydrides (e.g., $NaBH_4$, $LiBH_4$, $NaBH_3CN$) and aluminum hydrides (e.g., $LiAlH_4$) including, for example, $C_1$-$C_8$ alkyl aluminum hydrides, $C_2$-$C_{16}$ dialkyl aluminum hydrides, alkoxy aluminum hydrides (e.g., mono-, di-, and trialkoxy aluminum hydrides). Other suitable reducing agents include boranes such as $BH_3$ or $B_2H_6$ and adducts thereof. Example borane adducts include, for example, dialkylsulfide boranes (e.g., $BH_3$:$CH_3SCH_3$), amine boranes (e.g., $BH_3$:triethylamine), dialkyl ether boranes (e.g., $BH_3$:diethyl ether), cyclic ether boranes (e.g., $BH_3$:tetrahydrofuran), $C_1$-$C_8$ alkyl boranes, $C_2$-$C_{16}$ dialkyl boranes, $C_3$-$C_{24}$ trialkyl boranes (e.g., 9-borabicyclo[3.3.1]nonane), cyclic boranes (e.g., borolanes), and the like. Further example reducing agents include Red-Al and $H_2$ optionally in the presence of catalyst such as Pd/C.

As used herein, the term "cyclizing reagent" refers to any chemical reagent that can be used in a reaction to cyclize a linear or branched molecule or portion of a molecule. In some embodiments according to the present invention, cyclization of a linear or branched moiety attached to an aryl compound can be carried out using, for example, a Lewis acid. As is known in the art, a Lewis acid includes a molecule that can accept a lone pair of electrons. Example Lewis acids include hydrogen ion (a proton), boron derivatives such as $BH_3$ and $BF_3$, and aluminum derivatives such as $AlCl_3$. Some example Lewis acids include $C_1$-$C_8$ alkyl aluminum halide (e.g., methyl aluminum chloride, ethyl aluminum chloride, etc.), a $C_2$-$C_{16}$ dialkyl aluminum halide (e.g., dimethyl aluminum chloride, diethyl aluminum chloride, etc.), and trialkylaluminum.

In some embodiments, cyclizing can be carried out according to Friedel-Crafts alkylation chemistry which is known to follow the general transformation: $ArH+RCH_2Cl \rightarrow ArCH_2R$ (Ar is aryl and R is, for example, any alkyl, amino, or other group) in the presence of a reagent such as a Lewis acid. Friedel-Crafts reactions are typically carried out in the presence of $AlCl_3$ and optionally at elevated temperatures. Suitable Lewis acids include boron-containing reagents and aluminum containing reagents. Example boron-containing reagents include $BH_3$, $BF_3$ and adducts thereof (e.g., $BF_3$:TBME and $BF_3$:$OEt_2$). Example aluminum-containing reagents include alkyl aluminum halides, dialkyl aluminum halides, trialkyl aluminum, and aluminum halides (e.g., $AlCl_3$ and $AlBr_3$). Other suitable cyclizing reagents include, for example, acids such as sulfuric acid, sulfonic acids (e.g., $CF_3SO_3H$, $CH_3SO_3H$, pTSA), phosphoric acids, polyphosphoric acids (e.g., $H_3PO_4/P_2O_5$), and the like. Additional suitable Friedel-Crafts alkylation catalysts include $FeCl_3$, $TiCl_4$, $ZrCl_4$, and $ZnCl_4$.

As used herein, the term "halogenating/sulfonating reagent" refers to any chemical reagent that can be used to replace hydrogen or a chemical substituent on a molecule with a leaving group such as a halogen moiety or sulfonate moiety (e.g., alkyl sulfonate, mesylate, tosylate, etc.). In some embodiments, the halogenating/sulfonating reagent replaces a hydroxyl with a halogen moiety or sulfonate moiety. Example halogenating/sulfonating reagents include phosphorous trihalides (e.g., $PBr_3$), phosphorous pentahalides, phosphorous oxyhalides, thionyl halides (e.g., $SOBr_2$), and the like. Other halogenating/sulfonating reagents include N-bromosuccinimide (NBS), 1,3-dibromo-5,5-dimethylhydantoin, pyridinium tribromide (pyrHBr$_3$), diethylaminosulfur trifluoride (DAST), N-fluorobenzenesulfonimide, and the like. Further halogenating/sulfonating reagents include sulfonyl halides such as mesyl chloride, tosyl chloride, and the like.

As used herein, the term "leaving group" refers to a moiety that can be displaced by another moiety, such as by nucleophilic attack, during a chemical reaction. Leaving groups are well known in the art and include, for example, halogen, hydroxy, alkoxy, —O(CO)$R^a$, —OSO$_3$—$R^b$, and —OSi ($R^c$)$_3$ wherein $R^a$ can be $C_1$-$C_8$ alkyl, $C_3$-$C_7$ cycloalkyl, aryl, heteroaryl, or heterocycloalkyl, wherein $R^b$ can be $C_1$-$C_8$ alkyl, aryl (optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy), or heteroaryl (optionally substituted by one or more halo, cyano, nitro, $C_1$-$C_4$ alkyl, $C_1$-$C_4$ haloalkyl, $C_1$-$C_4$ alkoxy, or $C_1$-$C_4$ haloalkoxy), and wherein $R^c$ can be $C_1$-$C_8$ alkyl. Example leaving groups include chloro, bromo, iodo, mesylate, tosylate, trimethylsilyl, and the like.

As used herein, the terms "resolving" and "resolution" are used as known in the art and generally refer to the separation of a mixture of isomers such as stereoisomers (e.g., optical isomers such as enantiomers or diastereomers). Resolving can include processes that can increase the proportion of one stereoisomer over another in a mixture of stereoisomers. A mixture of stereoisomers having a greater proportion of a first stereoisomer over a further stereoisomer can be said to be "enriched" in the first stereoisomer.

As used herein, the term precipitating is used as known in the art and generally refers to the formation of solid (e.g., precipitate) from a solution in which the solid is dissolved. The solid can be amorphous, crystalline, or a mixture thereof. Methods of precipitation are well known in the art and include, for example, increasing the proportion of solvent in which a solute is insoluble, decreasing temperature, chemically transforming the solute such that it becomes no longer soluble in its solvent, and the like. Precipitation can be used to increase the proportion of a stereoisomer in a mixture of stereoisomers.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Green and Wuts, et al., *Protective Groups in Organic Synthesis,* 3rd. Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide can also be used as a solvent.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 20° C.) and "reduced temperature" refers to temperatures below room temperature.

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, camphoric acid, α-methoxy-α-trifluoromethylphenylacetic acid (MTPA or Mosher's acid), pyrrolidone-5-carboxylic acid, di-O-isopropylene-keto-glutamic acid, di-toluoyl-tartaric acid, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in *Remington's Pharmaceutical Sciences*, 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 2-(4-chlorophenyl)ethyl-N-2-chloropropionamide

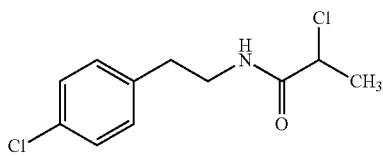

To a 1-liter, 3-necked round bottom flask under argon balloon equipped with reflux condenser and addition funnel, were added sequentially 2-(4-chlorophenyl)ethylamine (30 g, 193 mmol), 400 mL acetonitrile, triethylamine (19.5 g, 193 mmol) and 80 mL acetonitrile. The clear colorless solution was stirred and cooled to 0° C. 2-Chloropropionyl chloride (24.5 g, 193 mmol, distilled) in 5 mL acetonitrile was slowly added over 20 minutes to evolution of white gas, formation of white precipitate, and color change of reaction mixture to slight yellow. An additional 10 mL of acetonitrile was used to rinse the addition funnel. The mixture was stirred at 0° C. for 30 minutes and then warmed to room temperature and stirred vigorously for an additional one hour. The yellow reaction mixture was concentrated on the rotary evaporator to a solid containing triethylamine hydrochloride (76.36 grams). This material was taken up in 100 mL ethylacetate and 200 mL water, and stirred vigorously. The layers were separated and the aqueous layer was extracted with an additional 100 mL ethylacetate. The combined organic layers were washed twice with 25 mL of saturated brine, dried over magnesium sulfate, filtered, and concentrated to a light tan solid (41.6 grams, 88%). TLC in ethylacetate-hexane, 8:2 showed a major spot two-thirds of the way up the plate and a small spot at the baseline. Baseline spot was removed as follows: This material was taken up in 40 mL of ethylacetate and hexane was added until the solution became cloudy. Cooling to 0° C. produced a white crystalline solid (40.2 grams, 85% yield). The product is a known compound (Hasan et al., *Indian J. Chem.*, 1971, 9(9), 1022) with CAS Registry No. 34164-14-2.

LC/MS gave product 2.45 minute; 246.1 M$^+$+H$^+$.

$^1$H NMR (CDCl$_3$): δ 7.2 (dd, 4H, Ar), 6.7 (br S, 1H, NH), 4.38 (q, 1H, CHCH$_3$), 3.5 (q, 2H, ArCH$_2$CH$_2$NH), 2.8 (t, 2H, ArCH$_2$), 1.7 (d, 3H, CH$_3$).

$^{13}$C NMR (CDCl$_3$): 169 (1C, C=O), 136 (1C, Ar—Cl), 132 (1C, Ar), 130 (2C, Ar), 128 (2C, Ar), 56 (1C, CHCl), 40 (1C, CHN), 34 (1C, CHAr), 22 (1C, CH$_3$).

Example 2

Preparation of 8-chloro-1-methyl-2,3,4,5-tetrahydro-1H-3-benzazepin-2-one

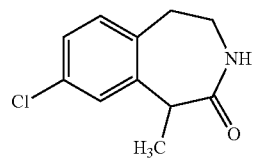

2-(4-Chlorophenyl)ethyl N-2-chloropropionamide (10 g, 40.6 mmol) of Example 1 and aluminum chloride (16 g, 119.9 mmol) were added to a clean dry 100 mL round bottom flask equipped with an argon balloon, stirring apparatus, and heating apparatus. The white solid melted to a tan oil with bubbling at 91° C. (Note: if impure starting materials are used, a black tar can result but clean product can still be isolated). The mixture was heated and stirred at 150° C. for 12 hours. (Note: The time is dependent on the reaction scale and can easily be followed by LC/MS; higher temperatures can be used for shorter time periods. E.g., a 1 gram sample was complete in 5 hours.) The reaction can be followed by LC/MS with the starting material at 2.45 minutes (246.1 M$^+$+H$^+$), the product at 2.24 minutes (209.6 M$^+$+H$^+$) on a 5 minute reaction time from 5-95% w/0.01% TFA in water/MeCN (50:50)

After cooling to room temperature, the reaction mixture was quenched with slow addition of 10 mL of MeOH followed by 5 mL of 5% HCl in water and 5 mL of ethyl acetate. After separation of the resulting layers, the aqueous layer was extracted a second time with 10 mL of ethyl acetate. The combined organic layers were dried over magnesium sulfate, filtered, and concentrated to a tan solid (6.78 grams, 80% yield). LC/MS showed one peak, at 2.2 min and 209.6 Ml.

This material was taken up in ethyl acetate, filtered through celite and Kieselgel 60 (0.5 inch plug on a 60 mL Buchner funnel) and the filtrate was recrystallized from hexane/ethyl acetate to give final product (4.61 grams, 54% yield).

$^1$H NMR (CDCl$_3$): 7.3-7.1 (m, 3H, Ar), 5.6 (br S, 1H, NH), 4.23 (q, 1H, CHCH$_3$), 3.8 (m, 1H, ArCH$_2$CH$_2$NH), 3.49 (m, 1H, ArCH$_2$CH$_2$NH), 3.48 (m, 1H, ArCH$_2$CH$_2$NH), 3.05 (m, 1H, ArCH$_2$CH$_2$NH), 1.6 (d, 3H, CH$_2$).

$^{13}$C NMR (CDCl$_3$): 178 (1C, C=O), 139 (1C, Ar), 135 (1C, Ar), 130, 129 (2C, Ar), 126 (2C, Ar), 42 (1C, C), 40 (1C, CHN), 33 (1C, CHAr), 14 (1C, CH$_3$).

Example 3

Preparation of 8-chloro-1-methyl-2,3,4,5-tetrahydro-1H-3-benzazepine

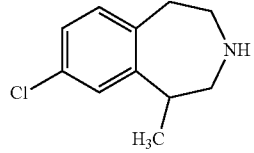

Procedure A

HPLC purified 8-chloro-1-methyl-2,3,4,5-tetrahydro-1H-3-benzazepin-2-one (150 mg, 0.716 mmol) of Example 2 was added to a 50 mL round bottom flask with 2M borane-tetrahydrofuran solution (2 mL, 2.15 mmol). The mixture was stirred 10 hours at room temperature under an argon balloon. LC/MS showed the desired product as the major peak with approximately 5% of starting material still present. The reaction mixture was quenched with 5 mL methanol and the solvents were removed on the rotary evaporator. This procedure was repeated with methanol addition and evaporation. The mixture was evaporated on the rotary evaporator followed by 2 hours in vacuo to give the product as a white solid (117 mg, 70% yield).

NMR, LC/MS and other analytical data are provided below.

Procedure B

Recrystallized 8-chloro-1-methyl-2,3,4,5-tetrahydro-1H-3-benzazapin-2-one (137 mg, 0.653 mmol) was added to a 50 mL round bottom task with stirring under nitrogen gas. To the flask was slowly added borane-tetrahydrofuran solution (1M, 10 mL) followed by boron trifluoride TBME solution (1 ml 8.85 mmol) with vigorous gas evolution. The mixture was stirred 6 hours at room temperature under nitrogen gas. LC/MS showed the desired product. The reaction mixture was quenched with 5 mL methanol and 3 mL conc. HCl and the solvents were removed on the rotary evaporator. This procedure was repeated with methanol and HCl addition and evaporation. The mixture was evaporated on the rotary evaporator followed by 2 hours on the pump to dryness to give 8-chloro-1-methyl-2,3,4,5-tetrahydro-1H-3-benzazapine hydrochloride (106 mg, 70% yield).

$^1$H NMR (CDCl$_3$): 10.2 (br s, 1H), 9.8 (br s, 1H), 7.14 (dd, 1H, J=2, 8 Hz), 7.11 (d, 1H, J=2 Hz), 7.03 (d, 1H, J=8 Hz), 3.6 (m, 2H), 3.5 (m, 2H), 2.8-3.0 (m, 3H), 1.5 (d, 3H, J=7 Hz).

LC/MS: 1.41 minute, 196.1 M+H$^+$ and 139 major fragment. No impurities were observed.

Example 4

Preparation of L-(+)-tartaric acid salt of (R)-8-chloro-1-methyl-2,3,4,5-tetrahydro-1H-3-benzazepine

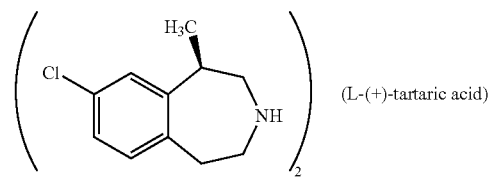

To a clean, dry 50 mL round bottom flask were added 11.5 g (0.06 mol) of 8-chloro-1-methyl-2,3,4,5-tetrahydro-1H-3-benzazepine from Example 3 to 2.23 g (0.015 mol) of L-(+)-tartaric acid. The suspension was diluted with 56 g of tert-butanol and 6.5 mL of H$_2$O. The mixture was heated to reflux (75-78° C.) and stirred for 10 min to obtain a colorless solution. The solution was slowly cooled down to room temperature (during 1 h) and stirred for 3 h at room temperature. The suspension was filtered and the residue was washed twice with acetone (10 mL). The product was dried under reduced pressure (50 mbar) at 60° C. to yield 6.3 g of the tartrate salt (ee=80). This tartrate salt was added to 56 g of tert-butanol and 6.5 mL of H$_2$O. The resulting suspension was heated to reflux and 1 to 2 g of H$_2$O was added to obtain a colorless solution. The solution was slowly cooled down to room temperature (over the course of 1 h) and stirred for 3 h at room temperature. The suspension was filtered and the residue was washed twice with acetone (10 mL). The product was dried under reduced pressure (50 mbar) at 60° C. to produce 4.9 g (48% yield) of product (ee>98.9).

If the ee value of the product obtained is not satisfactory, an additional recrystallization can be carried out as described. Either enantiomer can be synthesized in high ee utilizing this method.

Example 5

Conversion of Salt Form to Free Amine

The L-tartaric acid salt of 8-chloro-1-methyl-2,3,4,5-tetrahydro-1H-3-benzazepine (300 mg, 0.87 mmol) from Example 4 was added to a 25 mL round bottom flask with 50% sodium hydroxide solution (114 μL, 2.17 mmol) with an added 2 mL of water. The mixture was stirred 3 minutes at room temperature. The solution was extracted with methylene chloride (5 mL) twice. The combined organic extracts were washed with water (5 mL) and evaporated to dryness on the pump to get free amine (220 mg crude weight). LC/MS 196 (M+H).

Example 6

Preparation of 2-(4-Chlorophenyl)-N-ethyl-N-2-propylchloride

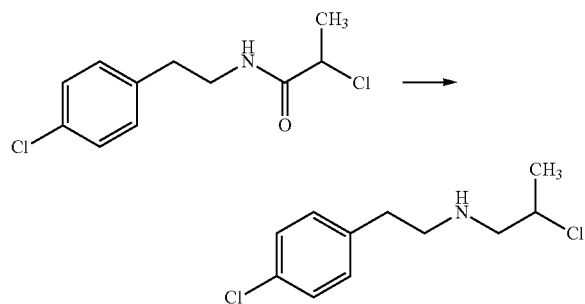

To a dry 100-milliliter, round bottom flask under nitrogen with stirring was added 2-(4-chlorophenyl)ethyl-N-2-chloro-propionylamide (8.8 g, 35.8 mmol) followed by borane in THF (1.8 M, 70 mL, 140 mmol) over 10 minutes (gas evolution and solid becomes solubilized). After the addition was complete, boron trifluoride in tert-butyl methyl ether (8 mL, 70.8 mmol) was added over 10 minutes with more gas evolution. After 4 hours, LC/MS showed complete reaction. The reaction mixture was quenched with 20 mL of conc. HCL (37%) with additional of gas evolution. The reaction mixture was stirred at 40° C. for 2 hours, cooled to room temperature and evaporated. Then, the white slurry was taken up in 40 mL ethyl acetate and 20 mL of 2.5 M NaOH to make a yellow solution over a white slurry. The yellow organic layer was washed with brine, dried over magnesium sulfate, filtered and evaporated to give 12.2 grams of white to yellow solid. This solid was recrystallized from ethyl acetate/hexane in two crops to give 6.7 grams of white solid product (80% yield).

$^1$H NMR (DMSO-d6): 9.0 (br s, 2H, NH, HCl), 7.2 (d, 2H, J=8 Hz), 7.05 (d, 2H, J=8 Hz), 4.5 (m, 1H), 3.2 (m, 2H), 3.1 (m, 2H), 3.0 (m, 2H), 1.5 (d, 3H, J=7 Hz).

LC/MS: 1.71 minute, 232.1 M+H$^+$ and 139 major fragment. Minor impurity observed at 2.46 min with 321 and 139 peaks.

Example 7

Preparation of 8-chloro-1-methyl-2,3,4,5-tetrahydro-1H-3-benzazepine

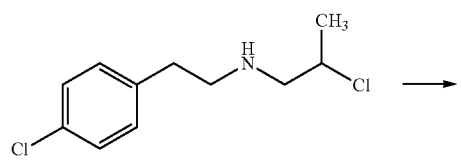

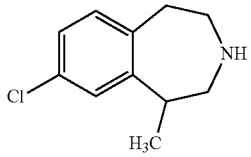

Small Scale 2-(4-Chlorophenyl)-N-ethyl-N-2-propylchloride (1 g, 4.3 mmol) of Example 6 was reacted with aluminum chloride (3 g, 22 mmol) in a dry 50 mL round bottom flask under nitrogen gas in an oil bath at 120° C. with stirring. Analysis by LC/MS showed complete reaction in two hours. After cooling the resulting black oil to room temperature, 20 mL ethyl acetate and 20 mL of pH 6 water were added. After 30 min of vigorous stirring the mixture was solubilized to a clear colorless upper organic layer and a brown clear lower aqueous layer. After separation of the layers, the aqueous layer was extracted two additional times with 20 mL ethyl acetate. The combined organic layers were dried over magnesium sulfate, filtered and evaporated to give 0.55 grams (55% yield) of a white to slightly yellow solid containing the HCl salt. This material was found to be very hygroscopic. The remaining aqueous layer (pH 6) was brought to pH 15 by addition of 5 grams of NaOH pellets. The aqueous layer became a thick white emulsion. Three times 40 mL of ethyl acetate were added to the thick white emulsion and decanted off. The combined organic layers were dried over magnesium sulfate, filtered and evaporated to give 0.3 g (36%) of a brown oil containing free amine. The combined yield was 91%.

$^1$H NMR (CDCl$_3$): 7.2 (d, 1H, J=2.5 Hz), 7.15 (dd, 1H, J=2.5, 8 Hz), 7.05 (d, 1H, J=8 Hz), 3.6 (m, 2H), 3.5 (m, 2H), 3.1 (m, 2H), 2.9 (m, 2H), 1.5 (d, 3H, J=7 Hz).

$^{13}$C NMR (CDCl$_4$): 144, 136, 133, 131, 127 (2), 51, 45, 32, 30, 17.

LC/MS: 1.41 minute, 196.1 M+H$^+$ and 139 major fragment. No impurities observed.

Large Scale 2-(4-Chlorophenyl)-N-ethyl-N-2-propylchloride (49.24 g, 179.92 mmol) and aluminum trichloride (34.79 g, 260.89 mmol) were added to a flask under a nitrogen atmosphere. To this solid mixture, 1,2-dichlorobenzene (139.31 g) was added resulting in a suspension which was then heated to 120° C. which was associated with evolution of hydrogen chloride gas, which was neutralized in a sodium hydroxide filled gas scrubber. The reaction mixture became a yellow to brown solution which was heated at 120° C. for a total of 12 hours. At the end of this time HPLC analysis indicated that the ratio of product to starting material was greater than 99:1 The reaction solution was cooled to 20 to 30° C. and added dropwise to a mixture of sodium hydroxide solution (176.0 g, 1320 mmol) approx. 30%, water (79.5 g), and cyclohexane (176 g), so that the internal temperature did not exceed 50° C. The layers were separated and the lower aqueous layer was extracted with cyclohexane (74 g). The combined organic layers were extracted with a solution of aq. hydrochloric acid (22.76 g, 231 mmol) 36/38% and water (68.23 g). The organic layer was extracted with water (45.47 g). The combined aqueous layers were washed with cyclohexane (37 g). To the aqueous layer was added sodium hydroxide (40.08 g, 301 mmol) solution approx. 30% and cyclohexane (100 g). The aqueous layer was extracted with cyclohexane (100 g). The combined organic layers were concentrated at 40° C. to 60° C. and a final vacuum of 30 mbar to give 36.79 g, of a yellow oil.

HPLC analysis indicated that the product had a purity of 85.45%, thus giving a corrected yield of 89.29%.

Example 8

Preparation of 2-(4-chlorophenyl)ethylbromide

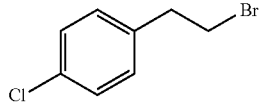

2-(4-Chlorophenyl)ethylbromide was prepared according to Robert, et al., *J. Org. Chem.*, 1987, 52, 5594).
Small Scale To a 100-milliliter, round bottom flask under nitrogen containing 2-(4-chlorophenyl)ethanol (10 g, 193 mmol) was added phosphorous tribromide (19 g, 193 mmol) via syringe while cooling 0° C. After the addition was complete, the ice bath was removed and the mixture was heated to 95° C. for two hours. The reaction mixture was quenched with slow addition of water in an ice bath. The material was taken up in 30 mL of methylene chloride, the layers were separated, and the organic layer was dried over magnesium sulfate, filtered, and evaporated to dryness to obtain 13.8 grams of clear oil (98% yield). LC/MS and proton NMR were as expected. $^1$H-NMR: 3.10 t, 3.51 t, 7.11 d, 7.26 d.
Large Scale To 171.05 g (1.092 mol) of 2-(4-chlorophenyl)ethanol was added dropwise 147.82 g (0.546 mol) of phosphorous tribromide over 3 hours and at a temperature of 0° C. The mixture was stirred at 0° C. for 15 min, at room temperature for 2 h, and then at 100° C. for 2 h, cooled to 0° C., hydrolized by dropwise addition of 400.0 g of water and diluted with 400.0 g of tert-butyl methyl ether. The organic layer was separated and washed with 100.0 g of water. The solvent was distilled off under reduced pressure to yield a colorless liquid. Yield: 95% (based on purity). Purity: 96%. Volume yield (reaction): 100.0%. Volume yield (extraction): 18.0%. $^1$H-NMR: 3.10 t, 3.51 t, 7.11 d, 7.26 d.

Example 9

Preparation of 2-(4-chlorophenyl)-N-ethyl-N-2-propanol

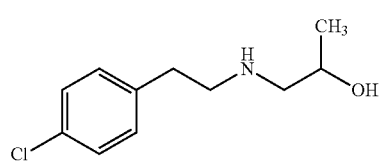

Small Scale

To 2-(4-chlorophenyl)ethylbromide (0.5 g, 2.8 mmol, from Example 8) in a 25 mL round bottom flask were added 1-amino-2-propanol (1.7 g, 22.8 mmol) dropwise via syringe at 95° C. The addition was carried out over one hour and the reaction mixture was stirred at 95° C. for an additional two hours. Then, the reaction mixture was cooled to room temperature and 3 mL of water were added, 10 mL of ethylacetate were added, and the organic layer was separated, dried over magnesium sulfate, filtered and concentrated to obtain 0.453 g of yellow solid (93% yield). LC/MS and proton NMR were as expected.
Large Scale To 821.25 g (10.93 mol) of 1-amino-2-propanol was added dropwise 240.01 g (1.093 mol) of 2-(4-chlorophenyl)ethylbromide during 3 hours and a temperature of 90-100° C. The mixture is stirred at 90-100° C. for further 1 h, cooled to room temperature, and diluted with 859.6 g of water. The water layer was extracted three times with 150.0 g of tert-butyl methyl ether. The combined organic phases were washed with 100.0 g of water, the solvent was distilled off at a temperature of 60° C. and reduced pressure to yield a colorless solid with a melting point of 68-70° C. Yield: 87% (based on purity). Purity: 99%. Volume yield (reaction): 21%. Volume yield (extraction): 12%. 1H-NMR: 1.12 d, 2.42 dd, 2.5-2.9 m, 2.62 d, 2.82 t, 3.75 m, 7.11 d, 7.23 d.

Example 10

Preparation of 2-(4-chlorophenyl)-N-ethyl-N-2-propylbromide

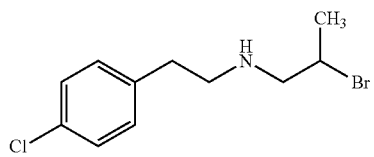

This preparation was based on Nagle et al., *Tetrahedron Letters*, 2000, 41, 3011.
Small Scale 2-(4-Chlorophenyl)-N-ethyl-N-2-propanol (453 mg, 2.12 mmol, see Example 9) was dissolved in 1.5 mL methylene chloride and dimethyl formamide (0.77 mL) was added to the solution. The reaction mixture was cooled to at 0° C. and thionyl bromide (0.23 mL, 3.0 mmol) was added dropwise. The reaction was then stirred at room temperature for two hours. The product precipitated. The mixture was cooled to 0° C. and the precipitate was filtered and washed with cold methylene chloride to obtain 350 mg of white solid. A second crop was obtained by concentrating, retaking up in methylene chloride, and cooling to obtain an additional 72 mg of product (56% yield).

$^1$H NMR (DMSO-d$_6$): 8.7 (br s, 1H), 8.6 (br s, 1H), 7.2 (d, 2H, J=8 Hz), 7.1 (d, 2H, J=8 Hz), 4.32 (m, 1H), 3.51 (br m, 1H), 3.28 m, (br m, 1H), 3.03 (m, 2H), 2.82 (m, 2H), 1.5 (d, 3H, J=7 Hz).

$^{13}$C NMR (DMSO-d$_6$): 136, 131, 130 (2), 128 (2), 53, 47, 44, 30, 23.

LC/MS: 1.56 min, 278 M+H$^+$ (—HBr) and 139 major fragment.
Large Scale 194.0 g (0.91 mol) of 2-(4-chlorophenyl)-N-ethyl-N-2-propanol were dissolved in 1000.0 g of CH$_2$Cl$_2$. Then 31.17 g (0.46 mol) of N,N-Dimethylformamide were added and the clear solution was cooled down to 0° C. At this temperature, 264.3 g (1.4 mol) of thionyl bromide were added within 1 h. After complete addition, the reaction mixture was allowed to warm up to room temperature and stirred for further 12 h, while precipitation of the product occurred. The reaction mixture was cooled to 0° C. and the precipitate was filtered off and washed with 500.0 g of ice-cold CH$_2$Cl$_2$, dried at 80° C. under reduced pressure to obtain an off-white powder with a melting point of 194-197° C. Yield: 63% (based on purity). Purity: 97%. Volume yield (reaction): 14%. $^1$H-NMR: 1.80 d, 3.05 m, 3.15 m, 3.45 m, 4.59 m, 7.15 d, 7.40 d, 8.95 s.

Example 11

Preparation of 2-(4-chlorophenyl)-N-ethyl-N-2-propylchloride

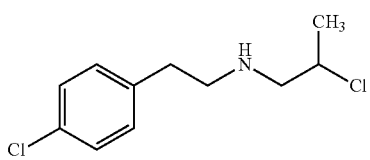

267 g (125 mmol) of 2-(4-chlorophenyl)-N-ethyl-N-2-propanol was diluted with 364 g of toluene and warmed to 40° C. 19.30 g, 222 mmol dimethylacetamide were added and following this 111.83 g 940 mmol thionyl chloride was added dropwise so that the internal temperature was kept between 40 and 60° C. The resulting thick suspension was stirred for 2 to 3 hours at 60 to 65° C. The suspension was filtered and washed with 335 g of toluene via the reactor. The resulting 397.1 g of a brown crude product was suspended in 326 g of isopropanol and 35.2 g of water, and heated to approx. 80 to 85° C. to reflux forming a clear brown solution. The solution was then cooled over 3 to 12 h to 0 to 5° C. and stirred for at least 1 hour at 0 to 5° C., before being centrifuged. The wet product was washed with 146 g of isopropanol in several parts via the reactor and with 100 g of isopropanol directly over the filter cake (when the material is still colored, the amount of isopropanol can be increased until colourless material is obtained). About 790 g of mother liquid with pH=0 was also formed. 157.93 g of a white to lightly beige wet product was yielded, which was dried at 70° C. in vacuum at 30 mbar. Yield: 113.42 g (99.53 percent by weight).

Example 12

Preparation of 8-chloro-1-methyl-2,3,4,5-tetrahydro-1H-3-benzazepine

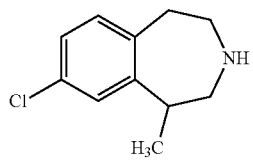

Small Scale

To 2-(4-chlorophenyl)-N-ethyl-N-2-propylbromide (0.343 g, 0.959 mmol, see Example 10) in a 50 mL round bottom flask was added aluminum chloride (0.192 g, 1.44 mmol). The two solids were heated at 140° C. for 4 hours and then cooled to 90° C. Toluene (350 microliters) was added and the reaction mixture was cooled to room temperature. Water (350 microliters) was added as well as 1 gram of ice. The mixture was stirred for 15 minutes then sodium hydroxide solution (350 microliters of a solution made up of 2 g of NaOH in 6 g water) was added. The reaction mixture was extracted three times with ethyl acetate. The organic layer was washed with brine, dried over magnesium sulfate and concentrated to give 218 mg of a dark yellow oil product (90% yield).

Attempted distillation of the oil product at 115-180° C. and 0.1 torr caused decomposition and dimerization.

LC/MS and proton NMR are as expected.

Large Scale

A 750 mL reaction vessel was charged with 2-(4-chlorophenyl)-N-ethyl-N-2-propylbromide (240 g, 0.67 mol) to which aluminum chloride (134 g, 1.01 mol) and 1,2-dichlorobenzene (480 g) were added. The resulting suspension was heated to 138-142° C. (yellow solution) and HBr-gas evolved (neutralized with sodium hydroxide solution). The reaction was stirred for 8-12 hours (monitored by HPLC). The reaction was cooled to 20-30° C. and transferred to a dropping funnel. Extraction mixture containing water (300 g), 30% sodium hydroxide solution (670 g), and cyclohexane (670 g) was added to the reaction vessel. The reaction solution was added portionwise to the extraction mixture while cooling keeping the temperature below 50° C. The resulting layers were separated and the aqueous phase was extracted with cyclohexane (144 g). The organic layers were combined and extracted with a solution of HCl (pH of the water layer was <2). The organic layer was extracted once more with water. The combined water layers were washed with cyclohexane. A 30% sodium hydroxide solution (100 g) was then added (pH of the water layer was >13). The water layer was first extracted with cyclohexane (720 g) and then with further cyclohexane (144 g). The combined organic layers were dried over sodium sulfate. The sodium sulfate was filtered out and the filtrate was evaporated under reduced pressure at a temperature of 45-50° C. Crude product was obtained as a glutinous oil (134.42 g).

Example 13

Large Scale Preparation of L-(+)-tartaric acid salt of (R)-8-chloro-1-methyl-2,4,5-tetrahydro-1H-3-benzazepine Crude product (134.32 g) of the large scale synthesis of Example 12 was dissolved in tert-butanol (480 g). An aqueous solution of L-(+)-tartaric acid (21 g of acid in 30 g of water) and seed crystals were added. The solution was stirred at 15-25° C. overnight until crystals formed. The resulting suspension was filtered and the precipitate washed with acetone. EE was 68.1% (HPLC). The precipitate was then refluxed in additional tert-butanol (480 g) and water (10 g). Water (80 g) was added until the precipitate dissolved completely and then the solution was cooled to 15-25° C. and stirred overnight. The resulting precipitate was filtered out and washed with acetone. EE was 96.8% (HPLC). The precipitate was again refluxed in additional tert-butanol (480 g) and stirred for 1 hour at reflux. The resulting suspension was cooled to 15-25° C. and stirred overnight. The resulting precipitate was filtered out and washed with acetone. EE was 98.7% (HPLC) and the product was dried under vacuum at 60° C. Yield was 34.96 g.

Example 14

Preparation of Hydrochloric Acid Salt of (R)-8-chloro-1-methyl-2,3,4,5-tetrahydro-1H-3-benzazepine To a clean, dry 25 mL round bottom flask were added (R)-8-chloro-1-methyl-2,3,4,5-tetrahydro-1H-3-benzazepine free amine (220 mg), 3 mL methylene chloride, and 1.74 mL of 1M HCl in ether. The mixture was stirred for 5 minutes at room temperature. The solvent was removed under reduced pressure to give a white solid, the HCl salt. The salt was re-dissolved in methylene chloride (3 mL) and an additional 1.74 mL of 1 M HCl was added and the solution was again stirred at room temperature for 5 minutes. The solvent was removed under reduced pressure to give the desired HCl salt of 8-chloro-1-methyl-2,3,4,5-tetrahydro-1H-3-benzazapine (190 mg crude weight, 95% yield). NMR data was consistent with the desired product.

$^1$H NMR (CDCl$_3$): 10.2 (hr s, 1H), 9.8 (br s, 1H), 7.14 (dd, 1H, J=2, 8 Hz), 7.11 (d, 1H, J=2 Hz), 7.03 (d, 1H, J=8 Hz), 3.6 (m, 2H), 3.5 (m, 2H), 2.8-3.0 (m, 3H), 1.5 (d, 3H, J=7 Hz).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A process for preparing a compound of Formula V:

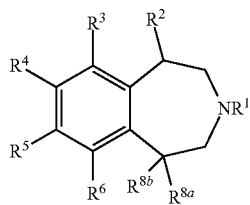

V or salt thereof,
wherein:
R$^1$ is H or C$_1$-C$_8$ alkyl;
R$^2$ is C$_1$-C$_8$ alkyl, —CH$_2$—O—(C$_1$-C$_8$ alkyl), C(O)O—(C$_1$-C$_8$ alkyl), —C(O)NH—(C$_1$-C$_8$ alkyl), or C$_1$-C$_4$ haloalkyl;
R$^3$, R$^4$, R$^5$, and R$^6$ are each, independently, H, halo, C$_1$-C$_8$ alkyl, C$_2$-C$_8$ alkenyl, C$_2$-C$_8$ alkynyl, C$_3$-C$_7$ cycloalkyl, C$_1$-C$_8$ haloalkyl, hydroxy, OR$^9$, alkoxyalkyl, C(O)-alkyl, C(O)O-alkyl, C(O)NH-alkyl, hydroxyalkyl, NR$^{10}$R$^{11}$, CN, NO$_2$, heterocycloalkyl, aryl, or heteroaryl, wherein said aryl and heteroaryl can be substituted with one or more substituents selected from C$_1$-C$_8$ alkyl, halo, C$_1$-C$_8$ haloalkyl, and alkoxy; or R$^4$ and R$^5$ together with the atoms to which they are attached form a 5- or 6-member heterocyclic ring having one O atom;
R$^{8a}$ and R$^{8b}$ are each, independently, H, halo, C$_1$-C$_8$ alkyl, C$_2$-C$_8$ alkenyl, C$_2$-C$_8$ alkynyl, C$_3$-C$_7$ cycloalkyl, C$_1$-C$_8$ haloalkyl, alkoxyalkyl, hydroxy, C(O)-alkyl, C(O)O-alkyl, C(O)NH-alkyl, or hydroxyalkyl, or R$^{8a}$ and R$^{8b}$ together with the carbon atom to which they are attached form a C$_3$-C$_7$ cycloalkyl group;
R$^9$ is H, C$_1$-C$_8$ alkyl, C$_2$-C$_8$ alkenyl, C$_2$-C$_8$ alkynyl, C$_3$-C$_7$ cycloalkyl, C$_1$-C$_8$ haloalkyl, aralkyl, aryl, heteroaryl, heteroarylalkyl, or allyl; and
R$^{10}$ and R$^{11}$ are each, independently, H, C$_1$-C$_8$ alkyl, C$_2$-C$_8$ alkenyl, C$_2$-C$_8$ alkynyl, C$_3$-C$_7$ cycloalkyl, C$_1$-C$_8$ haloalkyl, aralkyl, aryl, heteroaryl, heteroarylalkyl, or allyl, or R$^{10}$ and R$^{11}$ together with the N atom to which they are attached form a heterocyclic ring;

comprising the step of reacting a compound of Formula IX:

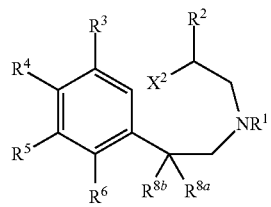

IX or salt thereof,
wherein X$^2$ is halo or SO$_2$R''; and R'' is C$_1$-C$_8$ alkyl, aryl, or heteroaryl each optionally substituted by one or more halo, cyano, nitro, C$_1$-C$_4$ alkyl, C$_1$-C$_4$ haloalkyl, C$_1$-C$_4$ alkoxy, or C$_1$-C$_4$ haloalkoxy,
with a cyclizing reagent for a time and under conditions suitable for forming said compound of Formula V.

2. A process according to claim 1, wherein said cyclizing reagent is AlCl$_3$.

3. A process according to claim 1, wherein the reaction of said compound of Formula IX with said cyclizing reagent is carried out in the presence of 1,2-dichlorobenzene.

4. A process according to claim 1, wherein the reaction of said compound of Formula IX with said cyclizing reagent is carried out at a temperature between 100 and 150° C.

5. A process according to claim 1, wherein X$^2$ is Cl.

6. A process according to claim 1, wherein X$^2$ is Br.

7. A process according to claim 1, wherein R$^1$ is H, R$^2$ is Me, R$^3$ is H, R$^4$ is Cl, R$^5$ is H, R$^6$ is H, R$^{8a}$ is H, and R$^{8b}$ is H.

8. A process according to claim 1, said process further comprising the step of forming said compound of Formula IX or salt thereof by reacting a compound of Formula X:

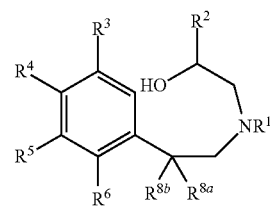

X or salt thereof;
with a halogenating/sulfonating reagent for a time and under conditions suitable for forming said compound of Formula IX or salt thereof.

9. A process according to claim 8, wherein said halogenating/sulfonating reagent is SOBr$_2$ or SOCl$_2$.

10. A process according to claim 8, wherein the reaction of said compound of Formula X with said halogenating/sulfonating reagent is carried out in the presence of solvent.

11. A process according to claim 10, wherein the reaction of said compound of Formula X with said halogenating/sulfonating reagent is carried out in the presence of solvent comprising dimethylformamide or toluene.

12. A process according to claim 8, said process further comprising the step of reacting a compound of Formula XI:

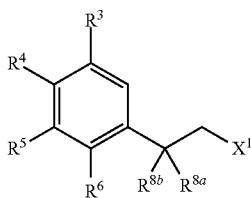

XI wherein $X^1$ is a leaving group,
with a compound of the following formula:

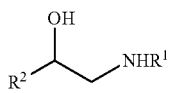

or salt thereof, for a time and under conditions suitable for forming said compound of Formula X or salt thereof.

13. A process according to claim 12, wherein $X^1$ is Br.

14. A process according to claim 12, wherein the reaction of said compound of Formula XI to give said compound of Formula X is carried out at a temperature from about 80 to about 110° C.

15. A process according to claim 8, said process further comprising the step of reacting a compound of Formula XII:

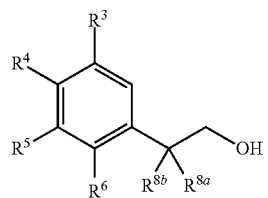

XII with a further halogenating/sulfonating reagent for a time and under conditions suitable for forming said compound of Formula XI.

16. A process according to claim 15, wherein said further halogenating/sulfonating reagent is $PBr_3$ or $PCl_3$.

17. A process according to claim 12, wherein $X^1$ is Cl.

18. A process according to claim 1, wherein:
$R^1$ is H, $R^2$ is Me, $R^3$ is H, $R^4$ is Cl, $R^5$ is H, $R^6$ is H, $R^{8a}$ is H, and $R^{8b}$ is H;
said cyclizing reagent is $AlCl_3$;
the reaction of said compound of Formula IX with said cyclizing reagent is carried out in the presence of 1,2-dichlorobenzene;
the reaction of said compound of Formula IX with said cyclizing reagent is carried out at a temperature between 100 and 150° C.; and
$X^2$ is Cl.

* * * * *